United States Patent [19]
Margolis et al.

[11] Patent Number: 5,625,040
[45] Date of Patent: Apr. 29, 1997

[54] PHOSPHACAN: A CHONDROITIN SULFATE PROTEOGLYCAN OF BRAIN THAT INTERACTS WITH NEURONS AND NEURAL CELL ADHESION MOLECULES

[75] Inventors: Richard U. Margolis; Renee K. Margolis; Patrice Maurel, all of New York, N.Y.

[73] Assignees: The Research Foundation of State University of New York, New York; New York University, Albany, both of N.Y.

[21] Appl. No.: 188,375

[22] Filed: Jan. 27, 1994

[51] Int. Cl.$^6$ .................. C07K 14/47; C07K 14/435; C07K 1/22; A61K 35/30
[52] U.S. Cl. .................. 530/395; 530/350; 530/413; 530/839; 424/570
[58] Field of Search .................. 530/395, 412, 530/413, 839, 330; 424/570

[56] References Cited

PUBLICATIONS

Gowda etal. "Chondroitin Sulfate & Heparan Sulfate Proteoglycans of PC12 Pheochromocytoma Cells" J. Biol. Chem. 264(19) 11436–11443 1989.
Krusius et al. "Primary Structure of an Extracellular Matrix Proteoglycan Core Protein Deduced fron Cloned cDNA" Proc. Natl. Acad. Sci 83 7683–7687 1986.
Oohira et al. "Inhibitory Effects of Brain Chondroitin Sulfate Proteoglycans on Neurite Outgrowth form PC 12D Cells" J. Neurosci. 11(3) 822–827 1991.
Margolis et al. "Nervous Tissue Proteoglycans" Experientia 49 429–446 1993.
Rauch, U. et al., "Isolation and Characterization of Developmentally Regulated Chondroitin Sulfate and Chondroitin/Keratan Sulfate Proteoglycans of Brain Identified with Monoclonal Antibodies" (1991) *J. Biol. Chem.* 266:14785–14801.
Grumet, M. et al., "Functional Characterization of Chondroitin Sulfate Proteoglycans of Brain: Interactions with Neurons and Neural Cell Adhesion Molecules" (1993) *J. Cell. Biol* 120:815–824.
Friedlander, D.R. et al., "Neurocan Binds With High Affinity to Ng–CAM and Inhibits Neuronal Adhesion and Neurite Outgrowth" (1993) *Soc. Neurosci. Abstr.* 19:626 (Abstr. 262.3).

Rauch, U. et al., "Cloning and Primary Structure of Neurocan, a Developmentally Regulated, Aggregating Chondroitin Sulfate Proteoglycan of Brain" (1992) *J. Biol. Chem.* 267:19536–19547.
Milev, P. et al., "Cellular Sites of Synthesis and Biological Activities of Brain Proteoglycans" (1993) *Glycobiology* 3, 535.
Milev, P. et al., "Interactions and Cellular Sites of Synthesis of Chondroitin Sulfate Proteoglycans of Brain" (1993) *J. Neurochem.* 61 (Suppl.):S110C.
Krusius, T. et al., "Identification of an O–Glycosidic Mannose–linked Sialylated Tetrasaccharide and Keratan Sulfate Oligosaccharides in the Chondroitin Sulfate Proteoglycan of Brain" (1986) *J. Biol. Chem.* 261:8237–8242.
Krusius, T. et al., "Structural Studies on Sialylated and Sulphated O–Glycosidic Mannose–linked Oligosaccharides in the Chondroitin Sulphate Proteoglycan of Brain" (1987) *Biochem. J.* 245:229–234.
Grumet, M., "Structure, Expression, and Function of Ng–CAM, a Member of the Immunoglobulin Superfamily Involved in Neuron–Neuron and Neuron–Glia Adhesion" (1992) *J. Neurosci. Res.* 31:1–13.
Reid, R.A. et al., "Variants of Human L1 Cell Adhesion Molecule Arise Through Alternate Splicing of RNA" (1992) *J. Mol. Neurosci.* 3:127–135.
Krueger et al., "A Human Transmembrane Protein–Tyrosine– Phosphatase, PTPepsilon, Is Expressed in Brain and Has a N–Terminal Receptor Domain Homologous to Carbonic Anhydrases", *Proc. Natl. Acad. Sci.* 89:7417–7421 (1992).
Levy et al., "The Cloning of a Receptor–type Protein Tyrosine Phosphatase Expressed in the Central Nervous System", *J. Biol. Chem.* 268:10573–10581 (1993).

*Primary Examiner*—Mindy Fleisher
*Assistant Examiner*—Nancy J. Degen
*Attorney, Agent, or Firm*—Morrison & Foerster LLP

[57] ABSTRACT

A phosphacan proteoglycan molecule, or a functional derivatives thereof, binds to brain cells and to a number of cell adhesion molecules including Ng-CAM and N-CAM. Such proteoglycan molecules or functional derivatives, as well as nucleic acids coding therefore are useful in treating a subject having a disorder associated with conditions where it is desirable to promote nerve regeneration. The compositions and methods of the present invention are also useful for diagnosing and monitoring human tumors such as gliomas and astrocytomas.

28 Claims, 8 Drawing Sheets

FIG. 1

N-terminus of 3F8 proteoglycan: YYRQQR<u>KLVEEIGW</u>SYTGALNQKNWGKK

N-terminus of 3H1 proteoglycan: YYRQQRKLVEEIGW - YTGALNQKN - GK - YP

3F8 CNBr peptide: DYL<u>QNNFREQQYK</u>FSRQVFSSYTGKEEIHEA (279-309)

3F8 endo Lys-C peptide: FAVLYQPLEGNDQTK (346-360)

Tryptic peptides from the 3F8 proteoglycan:
    FQGWEKPSLENTFIHNTG (82-99)
    FDADRF--FEE-VK-K--L (158-176)

Tryptic peptides from the 3H1 proteoglycan:
    FQGWEK (82-87)
    TVEINLTNDY (101-110)
    AIIDGTE (195-201)
    QVFSSYTGKEEIHEA (295-309)
    VVYDTMI (337-343)
    YSDQLIVDMPTEDAELDLFPELIGT (400-424)

FIG.2A

```
CCTAGACCCTGGCCAGTCACCGGCGTCCCCTGTCTCGGTGTTCCCACTCTCTGCACCCTA    60

AGCTGTACCCCTGCGGCTGGCGAGGGGCCGCGGACCCGGCTGGAGATGCGAATCCTGCAG    120
                                              M  R  I  L  Q     5

AGCTTCCTCGCGTGCGTTCAGCTACTGTGCGTGTGTCGCCTGGACTGGGCTTATGGATAC    180
 S  F  L  A  C  V  Q  L  L  C  V  C  R  L  D  W  A  Y  G  Y    25

TACAGACAACAGAGAAAACTTGTTGAAGAGATTGGCTGGTCCTATACAGGAGCACTAAAT    240
 Y  R  Q  Q  R  K  L  V  E  E  I  G  W  S  Y  T  G  A  L  N    45

CAAAAAAATTGGGGAAAGAAATATCCAATATGTAATAGCCCAAAGCAGTCTCCTATTAAT    300
 Q  K  N  W  G  K  K  Y  P  I  C  N  S  P  K  Q  S  P  I  N    65

ATTGATGAAGATCTTACACAAGTAAATGTGAATCTTAAGAAACTGAAATTTCAGGGTTGG    360
 I  D  E  D  L  T  Q  V  N  V  N  L  K  K  L  K  F  Q  G  W    85

GAAAAACCATCCTTGGAAAACACGTTTATTCACAACACTGGGAAAACAGTGGAAATAAAT    420
 E  K  P  S  L  E  N  T  F  I  H  N  T  G  K  T  V  E  I  N    105

CTCACCAATGACTACTATCTCAGTGGAGGACTTTCAGAAAAGGTCTTCAAGGCAAGCAAA    480
 L  T  N  D  Y  Y  L  S  G  G  L  S  E  K  V  F  K  A  S  K    125

ATGACTTTTCACTGGGGGAAATGCAATGTGTCATCGGAAGGATCGGAACACAGCTTAGAA    540
 M  T  F  H  W  G  K  C  N  V  S  S  E  G  S  E  H  S  L  E    145

GGGCAGAAGTTTCCACTCGAGATGCAAATCTACTGCTTCGATGCGGACCGATTTTCAAGT    600
 G  Q  K  F  P  L  E  M  Q  I  Y  C  F  D  A  D  R  F  S  S    165

TTTGAGGAAACAGTTAAAGGAAAAGGAAGGTTAAGGGCTCTATCCATTTTATTTGAGATT    660
 F  E  E  T  V  K  G  K  G  R  L  R  A  L  S  I  L  F  E  I    185

GGAGTTGAAGAAAATTTGGATTACAAAGCCATTATTGATGGGACTGAAAGTGTTAGTCGT    720
 G  V  E  E  N  L  D  Y  K  A  I  I  D  G  T  E  S  V  S  R    205

TTTGGAAAGCAGGCTGCCTTAGATCCGTTCATCTTGCAGAACCTCCTGCCAAACTCCACT    780
 F  G  K  Q  A  A  L  D  P  F  I  L  Q  N  L  L  P  N  S  T    225

GACAAGTACTACATTTACAACGGATCACTGACATCCCCTCCCTGCACAGACACCGTCGAA    840
 D  K  Y  Y  I  Y  N  G  S  L  T  S  P  P  C  T  D  T  V  E    245

TGGATTGTTTTTAAGGATACAGTTAGCATCTCTGAAAGCCAGCTGGCTGTATTTTGTGAA    900
 W  I  V  F  K  D  T  V  S  I  S  E  S  Q  L  A  V  F  C  E    265

GTTCTCACAATGCAACAGTCCGGGTATGTCATGTTGATGGATTACTTACAAAACAATTTC    960
 V  L  T  M  Q  Q  S  G  Y  V  M  L  M  D  Y  L  Q  N  N  F    285

CGAGAACAACAGTACAAGTTTTCCAGGCAGGTGTTTTCTTCGTACACTGGGAAGGAAGAG   1020
 R  E  Q  Q  Y  K  F  S  R  Q  V  F  S  S  Y  T  G  K  E  E    305
```

FIG. 2B

```
ATTCATGAAGCAGTGTGCAGTTCAGAACCAGAAAATGTGCAAGCTGACCCTGAGAATTAC 1080
 I  H  E  A  V  C  S  S  E  P  E  N  V  Q  A  D  P  E  N  Y   325

ACCAGCCTTCTGATCACATGGGAAAGGCCTCGGGTTGTTTATGACACAATGATTGAGAAG 1140
 T  S  L  L  I  T  W  E  R  P  R  V  V  Y  D  T  M  I  E  K   345

TTTGCGGTTCTGTACCAGCCACTGGAGGGAAACGACCAAACCAAGCATGAGTTTTTAACA 1200
 F  A  V  L  Y  Q  P  L  E  G  N  D  Q  T  K  H  E  F  L  T   365

GATGGCTATCAGGACTTGGGTGCCATTCTCAATAACTTAATACCTAACATGAGTTATGTG 1200
 D  G  Y  Q  D  L  G  A  I  L  N  N  L  I  P  N  M  S  Y  V   385

CTCCAAATAGTGGCCATATGCTCTAATGGCCTTTATGGAAAGTACAGTGACCAATTGATA 1320
 L  Q  I  V  A  I  C  S  N  G  L  Y  G  K  Y  S  D  Q  L  I   405

GTCGACATGCCTACTGAGGATGCTGAACTTGACCTCTTTCCTGAATTAATTGGAACTGAA 1380
 V  D  M  P  T  E  D  A  E  L  D  L  F  P  E  L  I  G  T  E   425

GAAATAATCAAGGAGGAAAACTATGGAAAAGGCAATGAAGAAGACACTGGCTTGAATCCC 1440
 E  I  I  K  E  E  N  Y  G  K  G  N  E  E  D  T  G  L  N  P   445

GGTAGAGACAGTGCCACAAACCAAATAAGGAAAAAGGAACCCCAGGTTTCTACCACAACT 1500
 G  R  D  S  A  T  N  Q  I  R  K  K  E  P  Q  V  S  T  T  T   465

CACTATAATCACATGGGGACTAAATATAATGAAGCCAAGACTAACCGATCTCCAACGAGA 1560
 H  Y  N  H  M  G  T  K  Y  N  E  A  K  T  N  R  S  P  T  R   485

GGATCTGAATTCTCTGGAAAGAGTGATGTTCTCAACACATCCCTGAATCCTACTTCCCAA 1620
 G  S  E  F  S  G  K  S  D  V  L  N  T  S  L  N  P  T  S  Q   505

CAGGTTGCTGAATTCAATCCAGAAAGAGAAATGTCCTTGCCTTCTCAGATTGGAACTAAC 1680
 Q  V  A  E  F  N  P  E  R  E  M  S  L  P  S  Q  I  G  T  N   525

CTGCCACCACACAGTGTGGAAGGCACCTCAGCCTCCTTAAACAGTGGCTCTAAAACTCTC 1740
 L  P  P  H  S  V  E  G  T  S  A  S  L  N  S  G  S  K  T  L   545

CTTGTCTTCCCACAGATGAACTTGTCTGGGACTGCAGAATCCTTAAATATGGTTTCCATA 1800
 L  V  F  P  Q  M  N  L  S  G  T  A  E  S  L  N  M  V  S  I   565

ACAGAGTACAAAGAGGTGTCTGCTGACCTCAGTGAGGAAGAAAACTTACTGACTGATTTC 1860
 T  E  Y  K  E  V  S  A  D  L  S  E  E  E  N  L  L  T  D  F   585

AAGCTCGATAGTGGAGCAGATGATTCGTCAGGCTCTAGCCCTGCATCCTCCACTGTCCCC 1920
 K  L  D  S  G  A  D  D  S  S  G  S  S  P  A  S  S  T  V  P   605

TTTTCCACAGATAATCTATCCCATGGATATACGTCTTCTTCAGACACGCCCGAGGCGGTC 1980
 F  S  T  D  N  L  S  H  G  Y  T  S  S  S  D  T  P  E  A  V   625

ACGTATGATGTCCTTAGGCCAGAATCTACGAGAAATGCTCTAGAGGATTCGGCTCCATCA 2040
 T  Y  D  V  L  R  P  E  S  T  R  N  A  L  E  D  S  A  P  S   645
```

FIG.2C

```
GGTTCAGAAGAATCACTAAAGGATCCCTCTCTTGAAGGGAGTGTGTGGTTCCCTGGATCC  2100
 G  S  E  E  S  L  K  D  P  S  L  E  G  S  V  W  F  P  G  S    665

ACAGACCTAACAACACAGTCTGAGACTGGATCTGGGAGAGAGGGCTTTCTCCAAGTTAAC  2160
 T  D  L  T  T  Q  S  E  T  G  S  G  R  E  G  F  L  Q  V  N    685

TCCACGGACTTCCAAGTTGATGAATCGAGGGAGACAACTGAGACATTTTCTCCAGATGCT  2220
 S  T  D  F  Q  V  D  E  S  R  E  T  T  E  T  F  S  P  D  A    705

ACCGCGTCCCGGGGTCCTTCGGTCACAGATATGGAAATGCCACATTATTCTACCTTTGCC  2280
 T  A  S  R  G  P  S  V  T  D  M  E  M  P  H  Y  S  T  F  A    725

TACCCCCCGACTGAAGTAACATCACATGCTTTCACTCCGTCCTCCAGACCACTTGATTTG  2340
 Y  P  P  T  E  V  T  S  H  A  F  T  P  S  S  R  P  L  D  L    745

GCTCCCACTAGCAACATCCTCCATTCGCAGACAACTCAACCAGTATACAATGGTGAGACA  2400
 A  P  T  S  N  I  L  H  S  Q  T  T  Q  P  V  Y  N  G  E  T    765

CCTCTTCAACCTTCCTACAGTAGTGAAGTCTTTCCTCTAGTCACCCCTTTGTTGCTTGAC  2460
 P  L  Q  P  S  Y  S  S  E  V  F  P  L  V  T  P  L  L  L  D    785

AATCAGACCCTCAACACTACCCCTGCTGCTTCAAGTAGTGATTCGGCCTTGCATGCTACG  2520
 N  Q  T  L  N  T  T  P  A  A  S  S  S  D  S  A  L  H  A  T    805

CCTGTATTCCCCAGTGTTGGTGTGTCATTTGACTCCATCCTGTCTTCCTATGATGATGCA  2580
 P  V  F  P  S  V  G  V  S  F  D  S  I  L  S  S  Y  D  D  A    825

CCTCTGCTCCCATTTTCCTCTGCTTCCTTCAGTAGTGACTTGTTTCACCATCTGCATACG  2640
 P  L  L  P  F  S  S  A  S  F  S  S  D  L  F  H  H  L  H  T    845

GTTTCTCAAACCCTTCCGCAAGTTACTTCAGCTGCTGAGAGGGATGAGCTGTCTTTGCAT  2700
 V  S  Q  T  L  P  Q  V  T  S  A  A  E  R  D  E  L  S  L  H    865

GCTTCTCTGCTGGTGGCTGGGGGTGATTTGCTGTTAGAGCCCAGCCTTGTTCAGTATTCT  2760
 A  S  L  L  V  A  G  G  D  L  L  L  E  P  S  L  V  Q  Y  S    885

GATGTGATGTCACATCAGGTCACTATTCATGCTGCTTCGGACACATTGGAATTTGGTAGT  2820
 D  V  M  S  H  Q  V  T  I  H  A  A  S  D  T  L  E  F  G  S    905

GAGTCTGCTGTCCTTTATAAAACGTCTATGGTTTCTCAAATCGAATCACCCAGCAGTGAT  2880
 E  S  A  V  L  Y  K  T  S  M  V  S  Q  I  E  S  P  S  S  D    925

GTCGTTATGCATGCATATTCGTCAGGGCCTGAAACTTCTTATGCCATTGAGGGCTCCCAC  2940
 V  V  M  H  A  Y  S  S  G  P  E  T  S  Y  A  I  E  G  S  H    945

CACGTGCTCACTGTTTCTTCCAGTTCTGCAATACCTGTGCATGATTCTGTCGGTGTAGCT  3000
 H  V  L  T  V  S  S  S  S  A  I  P  V  H  D  S  V  G  V  A    965

GATCAGGGGTCCTTACTTATCAATCCTAGCCATATATCACTGCCTGAGTCCTCATTTATT  3060
 D  Q  G  S  L  L  I  N  P  S  H  I  S  L  P  E  S  S  F  I    985
```

FIG.2D

```
ACTCCAACTGCATCATTACTGCAGCTTCCTCCTGCCCTCTCTGGTGATGGGGAGTGGTCT 3120
 T  P  T  A  S  L  L  Q  L  P  P  A  L  S  G  D  G  E  W  S    1005

GGAGCCTCCTCTGATAGTGAATTGCTTTTACCTGACACAGATGGGCTGAGAACTCTTAAC 3180
 G  A  S  S  D  S  E  L  L  L  P  D  T  D  G  L  R  T  L  N    1025

ATGTCTTCACCTGTTTCTGTAGCTGATTTTACATACACGACATCTGTGTCTGGCGATGAT 3240
 M  S  S  P  V  S  V  A  D  F  T  Y  T  T  S  V  S  G  D  D    1045

ATTAAGCCGCTTTCTAAAGGTGAAATGATGTATGGAAATGAGACCGAACTGAAAATGTCT 3300
 I  K  P  L  S  K  G  E  M  M  Y  G  N  E  T  E  L  K  M  S    1065

TCTTTCAGTGACATGGCATACCCTTCTAAAAGCACAGTCGTGCCAAAGATGTCTGATATT 3360
 S  F  S  D  M  A  Y  P  S  K  S  T  V  V  P  K  M  S  D  I    1085

GTAAATAAGTGGAGTGAATCTTTAAAAGAAACCTCTGTTTCCGTATCTAGCATAAACAGC 3420
 V  N  K  W  S  E  S  L  K  E  T  S  V  S  V  S  S  I  N  S    1105

GTGTTTACAGAGTCTCTTGTTTATCCCATAACTAAGGTTTTTGATCAGGAGATTAGTCGA 3480
 V  F  T  E  S  L  V  Y  P  I  T  K  V  F  D  Q  E  I  S  R    1125

GTTCCAGAGATTATCTTCCCAGTTAAACCTACACACACAGCATCTCAAGCATCTGGTGAC 3540
 V  P  E  I  I  F  P  V  K  P  T  H  T  A  S  Q  A  S  G  D    1145

ACTTGGCTTAAACCCGGGCTTAGCACAAACTCAGAGCCTGCGCTCTCTGACACTGCTTCT 3600
 T  W  L  K  P  G  L  S  T  N  S  E  P  A  L  S  D  T  A  S    1165

AGTGAAGTATCACACCCTTCAACACAGCCCTTGCTCTATGAGGCCGCATCTCCTTTTAAT 3660
 S  E  V  S  H  P  S  T  Q  P  L  L  Y  E  A  A  S  P  F  N    1185

ACGGAAGCATTGCTGCAACCTTCCTTTCCGGCTTCTGATGTTGACACCTTGCTTAAAACT 3720
 T  E  A  L  L  Q  P  S  F  P  A  S  D  V  D  T  L  L  K  T    1205

GCCCTTCCCTCTGGGCCTCGTGATCCAGTGCTGACTGAAACCCCCATGGTTGAGCAAAGT 3780
 A  L  P  S  G  P  R  D  P  V  L  T  E  T  P  M  V  E  Q  S    1225

AGCTCTTCCGTATCTCTTCCCCTGGCATCAGAGTCTGCTTCAAGCAAAAGCACGCTGCAC 3840
 S  S  S  V  S  L  P  L  A  S  E  S  A  S  S  K  S  T  L  H    1245

TTTACATCTGTACCAGTTCTCAATATGTCACCTTCTGATGTGCACCCCACTTCACTTCAA 3900
 F  T  S  V  P  V  L  N  M  S  P  S  D  V  H  P  T  S  L  Q    1265

CGCTTAACAGTTCCTCACTCGAGGGAGGAATATTTTGAACAAGGTTTGCTTAAGAGCAAA 3960
 R  L  T  V  P  H  S  R  E  E  Y  F  E  Q  G  L  L  K  S  K    1285

AGTCCCCAGCAAGTCCTGCCGTCCTTGCACAGCCATGACGAGTTTTTCCAAACTGCACAT 4020
 S  P  Q  Q  V  L  P  S  L  H  S  H  D  E  F  F  Q  T  A  H    1305

CTGGACATTAGCCAGGCCTACCCTCCAAAAGGAAGGCATGCATTTGCTACTCCTATTTTA 4080
 L  D  I  S  Q  A  Y  P  P  K  G  R  H  A  F  A  T  P  I  L    1325
```

FIG.2E

```
TCAATCAATGAACCACAAAATACACTTATAAACAGGCTTGTGTATTCTGAGGACATTTTC  4140
 S  I  N  E  P  Q  N  T  L  I  N  R  L  V  Y  S  E  D  I  F    1345

ATGCACCCTGAAATTTCTATTACTGATAAGGCACTTACTGGTCTACCAACGACCGTTTCT  4200
 M  H  P  E  I  S  I  T  D  K  A  L  T  G  L  P  T  T  V  S    1365

GATGTACTTATAGCTACTGACCATTCTGTTCCATTAGGAAGTGGGCCCATTTCCATGACA  4260
 D  V  L  I  A  T  D  H  S  V  P  L  G  S  G  P  I  S  M  T    1385

ACTGTTTCTCCCAACAGAGATGATTCTGTGACCACAACCAAGTTGCTTCTTCCTTCTAAA  4320
 T  V  S  P  N  R  D  D  S  V  T  T  T  K  L  L  P  S  K       1405

GCTACTTCTAAGCCGACTCATAGTGCCAGATCTGATGCCGATTTAGTAGGAGGTGGTGAA  4380
 A  T  S  K  P  T  H  S  A  R  S  D  A  D  L  V  G  G  E       1425

GATGGTGATGACTATGATGATGATGATTATGATGACATAGATAGTGATCGCTTTCCCGTA  4440
 D  G  D  D  Y  D  D  D  D  Y  D  D  I  D  S  D  R  F  P  V    1445

AATAAGTGTATGTCATGTTCACCCTATAGAGAATCACAGGAAAAGGTAATGAATGACTCG  4500
 N  K  C  M  S  C  S  P  Y  R  E  S  Q  E  K  V  M  N  D  S    1465

GACACCCAAGAAAGCAGTCTTGTGGATCAGAGTGACCCAATTTCACATTTGCTCTCTGAG  4560
 D  T  Q  E  S  S  L  V  D  Q  S  D  P  I  S  H  L  L  S  E    1485

AATACCGAAGAAGAAAATGGAGGCACGGGTGTAACTAGGGTGGATAAAAGTCCTGATAAG  4620
 N  T  E  E  E  N  G  G  T  G  V  T  R  V  D  K  S  P  D  K    1505

TCACCACCACCAAGTATGCTACCCCAGAAGCACAATGATGGAAGAGAGGACCGTGACATT  4680
 S  P  P  P  S  M  L  P  Q  K  H  N  D  G  R  E  D  R  D  I    1525

CAGATGGGTAGTGCTGTCCTTCCTCACACCCCAGGATCTAAAGCATGGGCAGTTTTGACA  4740
 Q  M  G  S  A  V  L  P  H  T  P  G  S  K  A  W  A  V  L  T    1545

AGTGATGAAGAGAGTGGGTCAGGGCAAGGCACCTCAGATAGCCTTAATGATAATGAGACT  4800
 S  D  E  E  S  G  S  G  Q  G  T  S  D  S  L  N  D  N  E  T    1565

TCCACAGATTTCAGTTTCCCAGATGTTAATGAAAAGGATGCTGATGGTGTCCTGGAAGCA  4860
 S  T  D  F  S  F  P  D  V  N  E  K  D  A  D  G  V  L  E  A    1585

GATGACACAGGCATAGCTCCGGGATCTCCACGGTCCTCCACACCATCTGTTACTAGTGGG  4920
 D  D  T  G  I  A  P  G  S  P  R  S  S  T  P  S  V  T  S  G    1605

CATTCAGGAGTATCCAACAGTTCAGAGGCAGGTTAGTTATGAGCAAAGGGATAGAACGAG  4980
 H  S  G  V  S  N  S  S  E  A  G  *                            1616

ATGTGCTGATTTTCTTGCTATGAAAGTAAAAATAGAAGAGTCACGGAAGAAAAGAATTCT  5040
GGTCCACCAGCAGATCTTCACTTTCTAATCAGAACGTTCAATACATTTATAGCTCTTATA  5100
AATATGGTTTTACTCATGATTTCGAATGAATATCCAACATATTTTGGTTATTGATTTTTA  5160
TTATCTTCAAAATGCATTGTGTGCTGTTACTAATCCCTATTCCTATTGTGTGTAGTATCA  5220
ACTATGTATGCATAATACGCCATTAGAATATTACAACGCAGTGTGCTGTGTTAAGACAGT  5280
TTAAATGTTCATACTTGTATTCTGAAACAAGTTGTACACAAACTCTATTGGATTTAAAAT  5340
```

FIG.2F

```
CTCAGTAATATGTCTATAAGCACCCATCCACCAATGGTGGACACTTCACATGTGCACAACA 5400
GCTTGGAGAGCTTCTCAAAGAACTACAGGGCTAAGATTTGATAGCTAAGGAAGTTTTT     5460
ATAAACATCATACTGCTTTTAAACTATCCTGAGCTTCTTTTGTTGCCTAAAGAGGGC       5520
AGTATAAACCACCAAAATACATTCTACTTGTGTTGTTACAGTATTCCAACTTACTAAT    5580
CGACATGAATATGCAGAAGATGCATAGGTATTGTATGACAAGATGTAAAAGAAAAGCCT    5640
ACAGCCTTTTCTGTAGAGATGCATTTCATTGTGTTAATATATTTATGCAATGGGTTTATT   5700
AGCCAGATGTTTCTTGGAGCAGACTGCAACCTAGAATACAGATGTGCTTTAAATGTCA     5760
ATGGTAACAAAATTCGAAATTCCATTAAGTGTTAAAAAAAAACTAGGTGATTCCATTG     5820
AATTCACGGCAAGATATTTAATTGCTTGATTAAGTGATGAGGTTTTTTTTAATGC       5880
ACAAGGAAAGTATTTAAATCTTAGCAAGTCAAAAGATAAGATAATGTATAATGTGACATT  5940
GGGTAATAATTGCACAGAGCTTAATATTAAAAATCCACAGTATAGAGCCAATCTCATTAA   6000
AATATATATTCCTTTGTTATTTCATCATTCACATTAGTTGTAAACTCTTTAGTATGGC    6060
AGCAATTAAGAGATTATATATTTAGATAAGACAGTTTCTTCTTTTCTGTATTCTGACGT   6120
GATCTCCACTTAACGTTCAGTTCAATTCAATATGAACTGATGTGTGAGAAGGAGTA     6180
ATGAGTCCATGGGTCACTGTAGTCAGGAATGTTGTTACATATGTGAATTGTTATCTGTCC  6240
TCAATTATAGCACTTGTTTTCTTCTATATTTTAGATTTATCTGAAAGGAAAGATCG      6300
TGAACATACTCTAATGGACAGACCATGCATATACACCAAAGCACTATATCTAGA        6360
ATTATCGAAGAAAGTTATTTCTCTTAGATGTACTAATTAGATTTATTAACTGTTAAGAG   6420
TAAGTTCCCCACTAATGAAGGGAGTAGGATCAAATAGAATTAGGAGAAACATCCATCTTCAGGAAATA 6480
ATACAGTTAAGCTGTATCTGTAAACTCATTATGGTACTTCTAAATGTAGAAAAACTGACATGATGTTTC 6540
TTAAAGCTGTATCTGTAAACTCATTATGGTACTTCTAAATGTAGAAAAACTGACATGATGTTTC 6600
TAGTCTGAAACTCATCATTTATGGCAAATATAGGCAAATATAGAGACTGTAAGATACTTG   6660
CTAAACTAATATAAAGAGTCCATCCAAAACTAACCCTGGGAATGTATTATTAGTGTCTG     6720
CTCTGGTTCCACATAAGAGTCCATCCAAAACTAACCCTGGGAATGTATTATTAGTGTCTG   6780
TCTCTTAGAACATGCTTACAT                                          6801
```

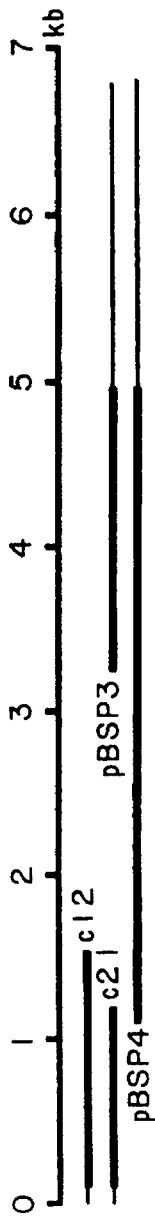

SEQUENCE LISTING ( 1 ) GENERAL INFORMATION:

( i i i ) NUMBER OF SEQUENCES: 21

( 2 ) INFORMATION FOR SEQ ID NO:1:

( i ) SEQUENCE CHARACTERISTICS:
        ( A ) LENGTH: 28 amino acids
        ( B ) TYPE: amino acid
        ( C ) STRANDEDNESS: single
        ( D ) TOPOLOGY: linear ( x i ) SEQUENCE DESCRIPTION: SEQ ID NO:1:

```
Tyr  Tyr  Arg  Gln  Gln  Arg  Lys  Leu  Val  Glu  Glu  Ile  Gly  Trp  Ser  Tyr
1                  5                           10                          15

Thr  Gly  Ala  Leu  Asn  Gln  Lys  Asn  Trp  Gly  Lys  Lys
               20                  25
```

( 2 ) INFORMATION FOR SEQ ID NO:2:

( i ) SEQUENCE CHARACTERISTICS:
        ( A ) LENGTH: 31 amino acids
        ( B ) TYPE: amino acid
        ( C ) STRANDEDNESS: single
        ( D ) TOPOLOGY: linear ( x i ) SEQUENCE DESCRIPTION: SEQ ID NO:2:

```
Asp  Tyr  Leu  Gln  Asn  Asn  Phe  Arg  Glu  Gln  Gln  Tyr  Lys  Phe  Ser  Arg
1                  5                           10                          15

Gln  Val  Phe  Ser  Ser  Tyr  Thr  Gly  Lys  Glu  Glu  Ile  His  Glu  Ala
               20                  25                          30
```

( 2 ) INFORMATION FOR SEQ ID NO:3:

( i ) SEQUENCE CHARACTERISTICS:
        ( A ) LENGTH: 18 amino acids
        ( B ) TYPE: amino acid
        ( C ) STRANDEDNESS: single
        ( D ) TOPOLOGY: linear ( x i ) SEQUENCE DESCRIPTION: SEQ ID NO:3:

```
Phe  Gln  Gly  Trp  Glu  Lys  Pro  Ser  Leu  Glu  Asn  Thr  Phe  Ile  His  Asn
1                  5                           10                          15

Thr  Gly
```

( 2 ) INFORMATION FOR SEQ ID NO:4:

( i ) SEQUENCE CHARACTERISTICS:
        ( A ) LENGTH: 13 amino acids
        ( B ) TYPE: amino acid
        ( C ) STRANDEDNESS: single
        ( D ) TOPOLOGY: linear ( x i ) SEQUENCE DESCRIPTION: SEQ ID NO:4:

```
Phe  Asp  Ala  Asp  Arg  Phe  Phe  Glu  Glu  Val  Lys  Lys  Leu
1                  5                           10
```

( 2 ) INFORMATION FOR SEQ ID NO:5:

( i ) SEQUENCE CHARACTERISTICS:
        ( A ) LENGTH: 15 amino acids
        ( B ) TYPE: amino acid
        ( C ) STRANDEDNESS: single
        ( D ) TOPOLOGY: linear ( x i ) SEQUENCE DESCRIPTION: SEQ ID NO:5:

Phe Ala Val Leu Tyr Gln Pro Leu Glu Gly Asn Asp Gln Thr Lys
1               5                   10                  15

( 2 ) INFORMATION FOR SEQ ID NO:6:

( i ) SEQUENCE CHARACTERISTICS:
      ( A ) LENGTH: 6801 base pairs
      ( B ) TYPE: nucleic acid
      ( C ) STRANDEDNESS: single
      ( D ) TOPOLOGY: linear ( i x ) FEATURE:
      ( A ) NAME/KEY: CDS
      ( B ) LOCATION: 106..4953

( x i ) SEQUENCE DESCRIPTION: SEQ ID NO:6:

| | | | | | |
|---|---|---|---|---|---|
| CCTAGACCCT | GGCCAGTCAC | CGGCGTCCCC | TGTCTCGGTG | TTCCCACTCT | CTGCACCCTA | 60 |
| AGCTGTACCC | CTGCGGCTGG | CGAGGGGCCG | CGGACCCGGC | TGGAG ATG CGA ATC | | 114 |

Met Arg Ile
                                                                                                 1

| | | | | | | | | | | | | | | | |
|---|---|---|---|---|---|---|---|---|---|---|---|---|---|---|---|
| CTG | CAG | AGC | TTC | CTC | GCG | TGC | GTT | CAG | CTA | CTG | TGC | GTG | TGT | CGC | CTG | 162 |
| Leu | Gln | Ser | Phe | Leu | Ala | Cys | Val | Gln | Leu | Leu | Cys | Val | Cys | Arg | Leu | |
| | | 5 | | | | | 10 | | | | | 15 | | | | |
| GAC | TGG | GCT | TAT | GGA | TAC | TAC | AGA | CAA | CAG | AGA | AAA | CTT | GTT | GAA | GAG | 210 |
| Asp | Trp | Ala | Tyr | Gly | Tyr | Tyr | Arg | Gln | Gln | Arg | Lys | Leu | Val | Glu | Glu | |
| 20 | | | | | 25 | | | | | 30 | | | | | 35 | |
| ATT | GGC | TGG | TCC | TAT | ACA | GGA | GCA | CTA | AAT | CAA | AAA | AAT | TGG | GGA | AAG | 258 |
| Ile | Gly | Trp | Ser | Tyr | Thr | Gly | Ala | Leu | Asn | Gln | Lys | Asn | Trp | Gly | Lys | |
| | | | | 40 | | | | | 45 | | | | | 50 | | |
| AAA | TAT | CCA | ATA | TGT | AAT | AGC | CCA | AAG | CAG | TCT | CCT | ATT | AAT | ATT | GAT | 306 |
| Lys | Tyr | Pro | Ile | Cys | Asn | Ser | Pro | Lys | Gln | Ser | Pro | Ile | Asn | Ile | Asp | |
| | | | | 55 | | | | | 60 | | | | | 65 | | |
| GAA | GAT | CTT | ACA | CAA | GTA | AAT | GTG | AAT | CTT | AAG | AAA | CTG | AAA | TTT | CAG | 354 |
| Glu | Asp | Leu | Thr | Gln | Val | Asn | Val | Asn | Leu | Lys | Lys | Leu | Lys | Phe | Gln | |
| | | | 70 | | | | | 75 | | | | | 80 | | | |
| GGT | TGG | GAA | AAA | CCA | TCC | TTG | GAA | AAC | ACG | TTT | ATT | CAC | AAC | ACT | GGG | 402 |
| Gly | Trp | Glu | Lys | Pro | Ser | Leu | Glu | Asn | Thr | Phe | Ile | His | Asn | Thr | Gly | |
| | 85 | | | | | 90 | | | | | 95 | | | | | |
| AAA | ACA | GTG | GAA | ATA | AAT | CTC | ACC | AAT | GAC | TAC | TAT | CTC | AGT | GGA | GGA | 450 |
| Lys | Thr | Val | Glu | Ile | Asn | Leu | Thr | Asn | Asp | Tyr | Tyr | Leu | Ser | Gly | Gly | |
| 100 | | | | | 105 | | | | | 110 | | | | | 115 | |
| CTT | TCA | GAA | AAG | GTC | TTC | AAG | GCA | AGC | AAA | ATG | ACT | TTT | CAC | TGG | GGG | 498 |
| Leu | Ser | Glu | Lys | Val | Phe | Lys | Ala | Ser | Lys | Met | Thr | Phe | His | Trp | Gly | |
| | | | | 120 | | | | | 125 | | | | | 130 | | |
| AAA | TGC | AAT | GTG | TCA | TCG | GAA | GGA | TCG | GAA | CAC | AGC | TTA | GAA | GGG | CAG | 546 |
| Lys | Cys | Asn | Val | Ser | Ser | Glu | Gly | Ser | Glu | His | Ser | Leu | Glu | Gly | Gln | |
| | | | 135 | | | | | 140 | | | | | 145 | | | |
| AAG | TTT | CCA | CTC | GAG | ATG | CAA | ATC | TAC | TGC | TTC | GAT | GCG | GAC | CGA | TTT | 594 |
| Lys | Phe | Pro | Leu | Glu | Met | Gln | Ile | Tyr | Cys | Phe | Asp | Ala | Asp | Arg | Phe | |
| | | 150 | | | | | 155 | | | | | 160 | | | | |
| TCA | AGT | TTT | GAG | GAA | ACA | GTT | AAA | GGA | AAA | GGA | AGG | TTA | AGG | GCT | CTA | 642 |
| Ser | Ser | Phe | Glu | Glu | Thr | Val | Lys | Gly | Lys | Gly | Arg | Leu | Arg | Ala | Leu | |
| | 165 | | | | | 170 | | | | | 175 | | | | | |
| TCC | ATT | TTA | TTT | GAG | ATT | GGA | GTT | GAA | GAA | AAT | TTG | GAT | TAC | AAA | GCC | 690 |
| Ser | Ile | Leu | Phe | Glu | Ile | Gly | Val | Glu | Glu | Asn | Leu | Asp | Tyr | Lys | Ala | |
| 180 | | | | | 185 | | | | | 190 | | | | | 195 | |
| ATT | ATT | GAT | GGG | ACT | GAA | AGT | GTT | AGT | CGT | TTT | GGA | AAG | CAG | GCT | GCC | 738 |
| Ile | Ile | Asp | Gly | Thr | Glu | Ser | Val | Ser | Arg | Phe | Gly | Lys | Gln | Ala | Ala | |
| | | | | 200 | | | | | 205 | | | | | 210 | | |
| TTA | GAT | CCG | TTC | ATC | TTG | CAG | AAC | CTC | CTG | CCA | AAC | TCC | ACT | GAC | AAG | 786 |

|     |     |     |     |     |     |     |     |     |     |     |     |     |     |     |     |      |
|-----|-----|-----|-----|-----|-----|-----|-----|-----|-----|-----|-----|-----|-----|-----|-----|------|
| Leu | Asp | Pro | Phe | Ile | Leu | Gln | Asn | Leu | Leu | Pro | Asn | Ser | Thr | Asp | Lys |      |
|     |     |     | 215 |     |     |     | 220 |     |     |     |     | 225 |     |     |     |      |
| TAC | TAC | ATT | TAC | AAC | GGA | TCA | CTG | ACA | TCC | CCT | CCC | TGC | ACA | GAC | ACC | 834  |
| Tyr | Tyr | Ile | Tyr | Asn | Gly | Ser | Leu | Thr | Ser | Pro | Pro | Cys | Thr | Asp | Thr |      |
|     |     | 230 |     |     |     | 235 |     |     |     |     | 240 |     |     |     |     |      |
| GTC | GAA | TGG | ATT | GTT | TTT | AAG | GAT | ACA | GTT | AGC | ATC | TCT | GAA | AGC | CAG | 882  |
| Val | Glu | Trp | Ile | Val | Phe | Lys | Asp | Thr | Val | Ser | Ile | Ser | Glu | Ser | Gln |      |
|     | 245 |     |     |     |     | 250 |     |     |     | 255 |     |     |     |     |     |      |
| CTG | GCT | GTA | TTT | TGT | GAA | GTT | CTC | ACA | ATG | CAA | CAG | TCC | GGG | TAT | GTC | 930  |
| Leu | Ala | Val | Phe | Cys | Glu | Val | Leu | Thr | Met | Gln | Gln | Ser | Gly | Tyr | Val |      |
| 260 |     |     |     | 265 |     |     |     |     | 270 |     |     |     |     | 275 |     |      |
| ATG | TTG | ATG | GAT | TAC | TTA | CAA | AAC | AAT | TTC | CGA | GAA | CAA | CAG | TAC | AAG | 978  |
| Met | Leu | Met | Asp | Tyr | Leu | Gln | Asn | Asn | Phe | Arg | Glu | Gln | Gln | Tyr | Lys |      |
|     |     |     |     | 280 |     |     |     |     | 285 |     |     |     |     | 290 |     |      |
| TTT | TCC | AGG | CAG | GTG | TTT | TCT | TCG | TAC | ACT | GGG | AAG | GAA | GAG | ATT | CAT | 1026 |
| Phe | Ser | Arg | Gln | Val | Phe | Ser | Ser | Tyr | Thr | Gly | Lys | Glu | Glu | Ile | His |      |
|     |     | 295 |     |     |     |     | 300 |     |     |     |     |     | 305 |     |     |      |
| GAA | GCA | GTG | TGC | AGT | TCA | GAA | CCA | GAA | AAT | GTG | CAA | GCT | GAC | CCT | GAG | 1074 |
| Glu | Ala | Val | Cys | Ser | Ser | Glu | Pro | Glu | Asn | Val | Gln | Ala | Asp | Pro | Glu |      |
|     |     | 310 |     |     |     |     | 315 |     |     |     | 320 |     |     |     |     |      |
| AAT | TAC | ACC | AGC | CTT | CTG | ATC | ACA | TGG | GAA | AGG | CCT | CGG | GTT | GTT | TAT | 1122 |
| Asn | Tyr | Thr | Ser | Leu | Leu | Ile | Thr | Trp | Glu | Arg | Pro | Arg | Val | Val | Tyr |      |
|     | 325 |     |     |     |     | 330 |     |     |     |     | 335 |     |     |     |     |      |
| GAC | ACA | ATG | ATT | GAG | AAG | TTT | GCG | GTT | CTG | TAC | CAG | CCA | CTG | GAG | GGA | 1170 |
| Asp | Thr | Met | Ile | Glu | Lys | Phe | Ala | Val | Leu | Tyr | Gln | Pro | Leu | Glu | Gly |      |
| 340 |     |     |     |     | 345 |     |     |     |     | 350 |     |     |     |     | 355 |      |
| AAC | GAC | CAA | ACC | AAG | CAT | GAG | TTT | TTA | ACA | GAT | GGC | TAT | CAG | GAC | TTG | 1218 |
| Asn | Asp | Gln | Thr | Lys | His | Glu | Phe | Leu | Thr | Asp | Gly | Tyr | Gln | Asp | Leu |      |
|     |     |     |     | 360 |     |     |     |     | 365 |     |     |     |     | 370 |     |      |
| GGT | GCC | ATT | CTC | AAT | AAC | TTA | ATA | CCT | AAC | ATG | AGT | TAT | GTG | CTC | CAA | 1266 |
| Gly | Ala | Ile | Leu | Asn | Asn | Leu | Ile | Pro | Asn | Met | Ser | Tyr | Val | Leu | Gln |      |
|     |     |     | 375 |     |     |     |     | 380 |     |     |     |     | 385 |     |     |      |
| ATA | GTG | GCC | ATA | TGC | TCT | AAT | GGC | CTT | TAT | GGA | AAG | TAC | AGT | GAC | CAA | 1314 |
| Ile | Val | Ala | Ile | Cys | Ser | Asn | Gly | Leu | Tyr | Gly | Lys | Tyr | Ser | Asp | Gln |      |
|     |     |     | 390 |     |     |     |     | 395 |     |     |     | 400 |     |     |     |      |
| TTG | ATA | GTC | GAC | ATG | CCT | ACT | GAG | GAT | GCT | GAA | CTT | GAC | CTC | TTT | CCT | 1362 |
| Leu | Ile | Val | Asp | Met | Pro | Thr | Glu | Asp | Ala | Glu | Leu | Asp | Leu | Phe | Pro |      |
|     | 405 |     |     |     |     | 410 |     |     |     |     | 415 |     |     |     |     |      |
| GAA | TTA | ATT | GGA | ACT | GAA | GAA | ATA | ATC | AAG | GAG | GAA | AAC | TAT | GGA | AAA | 1410 |
| Glu | Leu | Ile | Gly | Thr | Glu | Glu | Ile | Ile | Lys | Glu | Glu | Asn | Tyr | Gly | Lys |      |
| 420 |     |     |     |     | 425 |     |     |     |     | 430 |     |     |     |     | 435 |      |
| GGC | AAT | GAA | GAA | GAC | ACT | GGC | TTG | AAT | CCC | GGT | AGA | GAC | AGT | GCC | ACA | 1458 |
| Gly | Asn | Glu | Glu | Asp | Thr | Gly | Leu | Asn | Pro | Gly | Arg | Asp | Ser | Ala | Thr |      |
|     |     |     |     | 440 |     |     |     |     | 445 |     |     |     |     | 450 |     |      |
| AAC | CAA | ATA | AGG | AAA | AAG | GAA | CCC | CAG | GTT | TCT | ACC | ACA | ACT | CAC | TAT | 1506 |
| Asn | Gln | Ile | Arg | Lys | Lys | Glu | Pro | Gln | Val | Ser | Thr | Thr | Thr | His | Tyr |      |
|     |     |     | 455 |     |     |     |     | 460 |     |     |     |     | 465 |     |     |      |
| AAT | CAC | ATG | GGG | ACT | AAA | TAT | AAT | GAA | GCC | AAG | ACT | AAC | CGA | TCT | CCA | 1554 |
| Asn | His | Met | Gly | Thr | Lys | Tyr | Asn | Glu | Ala | Lys | Thr | Asn | Arg | Ser | Pro |      |
|     |     | 470 |     |     |     |     | 475 |     |     |     | 480 |     |     |     |     |      |
| ACG | AGA | GGA | TCT | GAA | TTC | TCT | GGA | AAG | AGT | GAT | GTT | CTC | AAC | ACA | TCC | 1602 |
| Thr | Arg | Gly | Ser | Glu | Phe | Ser | Gly | Lys | Ser | Asp | Val | Leu | Asn | Thr | Ser |      |
|     | 485 |     |     |     |     | 490 |     |     |     | 495 |     |     |     |     |     |      |
| CTG | AAT | CCT | ACT | TCC | CAA | CAG | GTT | GCT | GAA | TTC | AAT | CCA | GAA | AGA | GAA | 1650 |
| Leu | Asn | Pro | Thr | Ser | Gln | Gln | Val | Ala | Glu | Phe | Asn | Pro | Glu | Arg | Glu |      |
| 500 |     |     |     |     | 505 |     |     |     |     | 510 |     |     |     |     | 515 |      |
| ATG | TCC | TTG | CCT | TCT | CAG | ATT | GGA | ACT | AAC | CTG | CCA | CCA | CAC | AGT | GTG | 1698 |
| Met | Ser | Leu | Pro | Ser | Gln | Ile | Gly | Thr | Asn | Leu | Pro | Pro | His | Ser | Val |      |
|     |     |     |     | 520 |     |     |     |     | 525 |     |     |     |     | 530 |     |      |
| GAA | GGC | ACC | TCA | GCC | TCC | TTA | AAC | AGT | GGC | TCT | AAA | ACT | CTC | CTT | GTC | 1746 |

|  |  |  |  |  |  |  |  |  |  |  |  |  |  |  |  |
|---|---|---|---|---|---|---|---|---|---|---|---|---|---|---|---|
| Glu | Gly | Thr | Ser<br>535 | Ala | Ser | Leu | Asn | Ser<br>540 | Gly | Ser | Lys | Thr<br>545 | Leu | Leu | Val |

| TTC | CCA | CAG | ATG | AAC | TTG | TCT | GGG | ACT | GCA | GAA | TCC | TTA | AAT | ATG | GTT | 1794 |
|---|---|---|---|---|---|---|---|---|---|---|---|---|---|---|---|---|
| Phe | Pro | Gln<br>550 | Met | Asn | Leu | Ser | Gly<br>555 | Thr | Ala | Glu | Ser | Leu<br>560 | Asn | Met | Val |  |

| TCC | ATA | ACA | GAG | TAC | AAA | GAG | GTG | TCT | GCT | GAC | CTC | AGT | GAG | GAA | GAA | 1842 |
|---|---|---|---|---|---|---|---|---|---|---|---|---|---|---|---|---|
| Ser | Ile<br>565 | Thr | Glu | Tyr | Lys | Glu<br>570 | Val | Ser | Ala | Asp | Leu<br>575 | Ser | Glu | Glu | Glu |  |

| AAC | TTA | CTG | ACT | GAT | TTC | AAG | CTC | GAT | AGT | GGA | GCA | GAT | GAT | TCG | TCA | 1890 |
|---|---|---|---|---|---|---|---|---|---|---|---|---|---|---|---|---|
| Asn<br>580 | Leu | Leu | Thr | Asp | Phe<br>585 | Lys | Leu | Asp | Ser | Gly<br>590 | Ala | Asp | Asp | Ser | Ser<br>595 |  |

| GGC | TCT | AGC | CCT | GCA | TCC | TCC | ACT | GTC | CCC | TTT | TCC | ACA | GAT | AAT | CTA | 1938 |
|---|---|---|---|---|---|---|---|---|---|---|---|---|---|---|---|---|
| Gly | Ser | Ser | Pro | Ala<br>600 | Ser | Ser | Thr | Val | Pro<br>605 | Phe | Ser | Thr | Asp | Asn<br>610 | Leu |  |

| TCC | CAT | GGA | TAT | ACG | TCT | TCT | TCA | GAC | ACG | CCC | GAG | GCG | GTC | ACG | TAT | 1986 |
|---|---|---|---|---|---|---|---|---|---|---|---|---|---|---|---|---|
| Ser | His | Gly | Tyr<br>615 | Thr | Ser | Ser | Ser | Asp<br>620 | Thr | Pro | Glu | Ala | Val<br>625 | Thr | Tyr |  |

| GAT | GTC | CTT | AGG | CCA | GAA | TCT | ACG | AGA | AAT | GCT | CTA | GAG | GAT | TCG | GCT | 2034 |
|---|---|---|---|---|---|---|---|---|---|---|---|---|---|---|---|---|
| Asp | Val | Leu<br>630 | Arg | Pro | Glu | Ser | Thr<br>635 | Arg | Asn | Ala | Leu | Glu<br>640 | Asp | Ser | Ala |  |

| CCA | TCA | GGT | TCA | GAA | GAA | TCA | CTA | AAG | GAT | CCC | TCT | CTT | GAA | GGG | AGT | 2082 |
|---|---|---|---|---|---|---|---|---|---|---|---|---|---|---|---|---|
| Pro | Ser | Gly | Ser<br>645 | Glu | Glu | Ser | Leu | Lys<br>650 | Asp | Pro | Ser | Leu | Glu<br>655 | Gly | Ser |  |

| GTG | TGG | TTC | CCT | GGA | TCC | ACA | GAC | CTA | ACA | ACA | CAG | TCT | GAG | ACT | GGA | 2130 |
|---|---|---|---|---|---|---|---|---|---|---|---|---|---|---|---|---|
| Val<br>660 | Trp | Phe | Pro | Gly | Ser<br>665 | Thr | Asp | Leu | Thr | Thr<br>670 | Gln | Ser | Glu | Thr | Gly<br>675 |  |

| TCT | GGG | AGA | GAG | GGC | TTT | CTC | CAA | GTT | AAC | TCC | ACG | GAC | TTC | CAA | GTT | 2178 |
|---|---|---|---|---|---|---|---|---|---|---|---|---|---|---|---|---|
| Ser | Gly | Arg | Glu | Gly<br>680 | Phe | Leu | Gln | Val | Asn<br>685 | Ser | Thr | Asp | Phe | Gln<br>690 | Val |  |

| GAT | GAA | TCG | AGG | GAG | ACA | ACT | GAG | ACA | TTT | TCT | CCA | GAT | GCT | ACC | GCG | 2226 |
|---|---|---|---|---|---|---|---|---|---|---|---|---|---|---|---|---|
| Asp | Glu | Ser | Arg<br>695 | Glu | Thr | Thr | Glu | Thr<br>700 | Phe | Ser | Pro | Asp | Ala<br>705 | Thr | Ala |  |

| TCC | CGG | GGT | CCT | TCG | GTC | ACA | GAT | ATG | GAA | ATG | CCA | CAT | TAT | TCT | ACC | 2274 |
|---|---|---|---|---|---|---|---|---|---|---|---|---|---|---|---|---|
| Ser | Arg | Gly | Pro<br>710 | Ser | Val | Thr | Asp | Met<br>715 | Glu | Met | Pro | His | Tyr<br>720 | Ser | Thr |  |

| TTT | GCC | TAC | CCC | CCG | ACT | GAA | GTA | ACA | TCA | CAT | GCT | TTC | ACT | CCG | TCC | 2322 |
|---|---|---|---|---|---|---|---|---|---|---|---|---|---|---|---|---|
| Phe | Ala | Tyr<br>725 | Pro | Pro | Thr | Glu | Val<br>730 | Thr | Ser | His | Ala | Phe<br>735 | Thr | Pro | Ser |  |

| TCC | AGA | CCA | CTT | GAT | TTG | GCT | CCC | ACT | AGC | AAC | ATC | CTC | CAT | TCG | CAG | 2370 |
|---|---|---|---|---|---|---|---|---|---|---|---|---|---|---|---|---|
| Ser | Arg | Pro | Leu | Asp<br>740 | Leu | Ala | Pro | Thr | Ser<br>745 | Asn | Ile | Leu | His | Ser<br>750 | Gln |  |

| ACA | ACT | CAA | CCA | GTA | TAC | AAT | GGT | GAG | ACA | CCT | CTT | CAA | CCT | TCC | TAC | 2418 |
|---|---|---|---|---|---|---|---|---|---|---|---|---|---|---|---|---|
| Thr<br>740 | Thr | Gln | Pro | Val | Tyr<br>760 | Asn | Gly | Glu | Thr | Pro<br>765 | Leu | Gln | Pro | Ser | Tyr<br>770 |  |

| AGT | AGT | GAA | GTC | TTT | CCT | CTA | GTC | ACC | CCT | TTG | TTG | CTT | GAC | AAT | CAG | 2466 |
|---|---|---|---|---|---|---|---|---|---|---|---|---|---|---|---|---|
| Ser | Ser | Glu | Val<br>775 | Phe | Pro | Leu | Val | Thr<br>780 | Pro | Leu | Leu | Leu | Asp<br>785 | Asn | Gln |  |

| ACC | CTC | AAC | ACT | ACC | CCT | GCT | GCT | TCA | AGT | AGT | GAT | TCG | GCC | TTG | CAT | 2514 |
|---|---|---|---|---|---|---|---|---|---|---|---|---|---|---|---|---|
| Thr | Leu | Asn<br>790 | Thr | Thr | Pro | Ala | Ala<br>795 | Ser | Ser | Ser | Asp | Ser<br>800 | Ala | Leu | His |  |

| GCT | ACG | CCT | GTA | TTC | CCC | AGT | GTT | GGT | GTG | TCA | TTT | GAC | TCC | ATC | CTG | 2562 |
|---|---|---|---|---|---|---|---|---|---|---|---|---|---|---|---|---|
| Ala | Thr<br>805 | Pro | Val | Phe | Pro<br>810 | Ser | Val | Gly | Val | Ser<br>815 | Phe | Asp | Ser | Ile | Leu |  |

| TCT | TCC | TAT | GAT | GAT | GCA | CCT | CTG | CTC | CCA | TTT | TCC | TCT | GCT | TCC | TTC | 2610 |
|---|---|---|---|---|---|---|---|---|---|---|---|---|---|---|---|---|
| Ser<br>820 | Ser | Tyr | Asp | Asp | Ala<br>825 | Pro | Leu | Leu | Pro<br>830 | Phe | Ser | Ser | Ala | Ser<br>835 | Phe |  |

| AGT | AGT | GAC | TTG | TTT | CAC | CAT | CTG | CAT | ACG | GTT | TCT | CAA | ACC | CTT | CCG | 2658 |
|---|---|---|---|---|---|---|---|---|---|---|---|---|---|---|---|---|
| Ser | Ser | Asp | Leu | Phe<br>840 | His | His | Leu | His<br>845 | Thr | Val | Ser | Gln | Thr<br>850 | Leu | Pro |  |

| CAA | GTT | ACT | TCA | GCT | GCT | GAG | AGG | GAT | GAG | CTG | TCT | TTG | CAT | GCT | TCT | 2706 |
|---|---|---|---|---|---|---|---|---|---|---|---|---|---|---|---|---|

|  |  |  |  |  |  |  |  |  |  |  |  |  |  |  |  |  |
|---|---|---|---|---|---|---|---|---|---|---|---|---|---|---|---|---|
| Gln | Val | Thr | Ser | Ala | Ala | Glu | Arg | Asp | Glu | Leu | Ser | Leu | His | Ala | Ser |  |
|  |  |  | 855 |  |  |  | 860 |  |  |  |  |  | 865 |  |  |  |

| CTG | CTG | GTG | GCT | GGG | GGT | GAT | TTG | CTG | TTA | GAG | CCC | AGC | CTT | GTT | CAG | 2754 |
|---|---|---|---|---|---|---|---|---|---|---|---|---|---|---|---|---|
| Leu | Leu | Val | Ala | Gly | Gly | Asp | Leu | Leu | Leu | Glu | Pro | Ser | Leu | Val | Gln |  |
|  |  | 870 |  |  |  |  | 875 |  |  |  |  | 880 |  |  |  |  |

| TAT | TCT | GAT | GTG | ATG | TCA | CAT | CAG | GTC | ACT | ATT | CAT | GCT | GCT | TCG | GAC | 2802 |
|---|---|---|---|---|---|---|---|---|---|---|---|---|---|---|---|---|
| Tyr | Ser | Asp | Val | Met | Ser | His | Gln | Val | Thr | Ile | His | Ala | Ala | Ser | Asp |  |
|  | 885 |  |  |  |  | 890 |  |  |  |  | 895 |  |  |  |  |  |

| ACA | TTG | GAA | TTT | GGT | AGT | GAG | TCT | GCT | GTC | CTT | TAT | AAA | ACG | TCT | ATG | 2850 |
|---|---|---|---|---|---|---|---|---|---|---|---|---|---|---|---|---|
| Thr | Leu | Glu | Phe | Gly | Ser | Glu | Ser | Ala | Val | Leu | Tyr | Lys | Thr | Ser | Met |  |
| 900 |  |  |  |  | 905 |  |  |  |  | 910 |  |  |  |  | 915 |  |

| GTT | TCT | CAA | ATC | GAA | TCA | CCC | AGC | AGT | GAT | GTC | GTT | ATG | CAT | GCA | TAT | 2898 |
|---|---|---|---|---|---|---|---|---|---|---|---|---|---|---|---|---|
| Val | Ser | Gln | Ile | Glu | Ser | Pro | Ser | Ser | Asp | Val | Val | Met | His | Ala | Tyr |  |
|  |  |  |  | 920 |  |  |  |  | 925 |  |  |  |  | 930 |  |  |

| TCG | TCA | GGG | CCT | GAA | ACT | TCT | TAT | GCC | ATT | GAG | GGC | TCC | CAC | CAC | GTG | 2946 |
|---|---|---|---|---|---|---|---|---|---|---|---|---|---|---|---|---|
| Ser | Ser | Gly | Pro | Glu | Thr | Ser | Tyr | Ala | Ile | Glu | Gly | Ser | His | His | Val |  |
|  |  |  | 935 |  |  |  |  | 940 |  |  |  |  | 945 |  |  |  |

| CTC | ACT | GTT | TCT | TCC | AGT | TCT | GCA | ATA | CCT | GTG | CAT | GAT | TCT | GTC | GGT | 2994 |
|---|---|---|---|---|---|---|---|---|---|---|---|---|---|---|---|---|
| Leu | Thr | Val | Ser | Ser | Ser | Ser | Ala | Ile | Pro | Val | His | Asp | Ser | Val | Gly |  |
|  |  | 950 |  |  |  |  | 955 |  |  |  |  | 960 |  |  |  |  |

| GTA | GCT | GAT | CAG | GGG | TCC | TTA | CTT | ATC | AAT | CCT | AGC | CAT | ATA | TCA | CTG | 3042 |
|---|---|---|---|---|---|---|---|---|---|---|---|---|---|---|---|---|
| Val | Ala | Asp | Gln | Gly | Ser | Leu | Leu | Ile | Asn | Pro | Ser | His | Ile | Ser | Leu |  |
| 965 |  |  |  |  | 970 |  |  |  |  | 975 |  |  |  |  |  |  |

| CCT | GAG | TCC | TCA | TTT | ATT | ACT | CCA | ACT | GCA | TCA | TTA | CTG | CAG | CTT | CCT | 3090 |
|---|---|---|---|---|---|---|---|---|---|---|---|---|---|---|---|---|
| Pro | Glu | Ser | Ser | Phe | Ile | Thr | Pro | Thr | Ala | Ser | Leu | Leu | Gln | Leu | Pro |  |
| 980 |  |  |  |  | 985 |  |  |  |  | 990 |  |  |  |  | 995 |  |

| CCT | GCC | CTC | TCT | GGT | GAT | GGG | GAG | TGG | TCT | GGA | GCC | TCC | TCT | GAT | AGT | 3138 |
|---|---|---|---|---|---|---|---|---|---|---|---|---|---|---|---|---|
| Pro | Ala | Leu | Ser | Gly | Asp | Gly | Glu | Trp | Ser | Gly | Ala | Ser | Ser | Asp | Ser |  |
|  |  |  |  | 1000 |  |  |  |  | 1005 |  |  |  |  | 1010 |  |  |

| GAA | TTG | CTT | TTA | CCT | GAC | ACA | GAT | GGG | CTG | AGA | ACT | CTT | AAC | ATG | TCT | 3186 |
|---|---|---|---|---|---|---|---|---|---|---|---|---|---|---|---|---|
| Glu | Leu | Leu | Leu | Pro | Asp | Thr | Asp | Gly | Leu | Arg | Thr | Leu | Asn | Met | Ser |  |
|  |  |  | 1015 |  |  |  |  | 1020 |  |  |  |  | 1025 |  |  |  |

| TCA | CCT | GTT | TCT | GTA | GCT | GAT | TTT | ACA | TAC | ACG | ACA | TCT | GTG | TCT | GGC | 3234 |
|---|---|---|---|---|---|---|---|---|---|---|---|---|---|---|---|---|
| Ser | Pro | Val | Ser | Val | Ala | Asp | Phe | Thr | Tyr | Thr | Thr | Ser | Val | Ser | Gly |  |
|  |  | 1030 |  |  |  |  | 1035 |  |  |  |  | 1040 |  |  |  |  |

| GAT | GAT | ATT | AAG | CCG | CTT | TCT | AAA | GGT | GAA | ATG | ATG | TAT | GGA | AAT | GAG | 3282 |
|---|---|---|---|---|---|---|---|---|---|---|---|---|---|---|---|---|
| Asp | Asp | Ile | Lys | Pro | Leu | Ser | Lys | Gly | Glu | Met | Met | Tyr | Gly | Asn | Glu |  |
| 1045 |  |  |  |  | 1050 |  |  |  |  | 1055 |  |  |  |  |  |  |

| ACC | GAA | CTG | AAA | ATG | TCT | TCT | TTC | AGT | GAC | ATG | GCA | TAC | CCT | TCT | AAA | 3330 |
|---|---|---|---|---|---|---|---|---|---|---|---|---|---|---|---|---|
| Thr | Glu | Leu | Lys | Met | Ser | Ser | Phe | Ser | Asp | Met | Ala | Tyr | Pro | Ser | Lys |  |
| 1060 |  |  |  |  | 1065 |  |  |  |  | 1070 |  |  |  |  | 1075 |  |

| AGC | ACA | GTC | GTG | CCA | AAG | ATG | TCT | GAT | ATT | GTA | AAT | AAG | TGG | AGT | GAA | 3378 |
|---|---|---|---|---|---|---|---|---|---|---|---|---|---|---|---|---|
| Ser | Thr | Val | Val | Pro | Lys | Met | Ser | Asp | Ile | Val | Asn | Lys | Trp | Ser | Glu |  |
|  |  |  |  | 1080 |  |  |  |  | 1085 |  |  |  |  | 1090 |  |  |

| TCT | TTA | AAA | GAA | ACC | TCT | GTT | TCC | GTA | TCT | AGC | ATA | AAC | AGC | GTG | TTT | 3426 |
|---|---|---|---|---|---|---|---|---|---|---|---|---|---|---|---|---|
| Ser | Leu | Lys | Glu | Thr | Ser | Val | Ser | Val | Ser | Ser | Ile | Asn | Ser | Val | Phe |  |
|  |  |  | 1095 |  |  |  |  | 1100 |  |  |  |  | 1105 |  |  |  |

| ACA | GAG | TCT | CTT | GTT | TAT | CCC | ATA | ACT | AAG | GTT | TTT | GAT | CAG | GAG | ATT | 3474 |
|---|---|---|---|---|---|---|---|---|---|---|---|---|---|---|---|---|
| Thr | Glu | Ser | Leu | Val | Tyr | Pro | Ile | Thr | Lys | Val | Phe | Asp | Gln | Glu | Ile |  |
|  |  | 1110 |  |  |  |  | 1115 |  |  |  |  | 1120 |  |  |  |  |

| AGT | CGA | GTT | CCA | GAG | ATT | ATC | TTC | CCA | GTT | AAA | CCT | ACA | CAC | ACA | GCA | 3522 |
|---|---|---|---|---|---|---|---|---|---|---|---|---|---|---|---|---|
| Ser | Arg | Val | Pro | Glu | Ile | Ile | Phe | Pro | Val | Lys | Pro | Thr | His | Thr | Ala |  |
|  | 1125 |  |  |  |  | 1130 |  |  |  |  | 1135 |  |  |  |  |  |

| TCT | CAA | GCA | TCT | GGT | GAC | ACT | TGG | CTT | AAA | CCC | GGG | CTT | AGC | ACA | AAC | 3570 |
|---|---|---|---|---|---|---|---|---|---|---|---|---|---|---|---|---|
| Ser | Gln | Ala | Ser | Gly | Asp | Thr | Trp | Leu | Lys | Pro | Gly | Leu | Ser | Thr | Asn |  |
| 1140 |  |  |  |  | 1145 |  |  |  |  | 1150 |  |  |  |  | 1155 |  |

| TCA | GAG | CCT | GCG | CTC | TCT | GAC | ACT | GCT | TCT | AGT | GAA | GTA | TCA | CAC | CCT | 3618 |
|---|---|---|---|---|---|---|---|---|---|---|---|---|---|---|---|---|
| Ser | Glu | Pro | Ala | Leu | Ser | Asp | Thr | Ala | Ser | Ser | Glu | Val | Ser | His | Pro |  |
|  |  |  |  | 1160 |  |  |  |  | 1165 |  |  |  |  | 1170 |  |  |

| TCA | ACA | CAG | CCC | TTG | CTC | TAT | GAG | GCC | GCA | TCT | CCT | TTT | AAT | ACG | GAA | 3666 |
|---|---|---|---|---|---|---|---|---|---|---|---|---|---|---|---|---|

|  |  |  |  |  |  |  |  |  |  |  |  |  |  |  |  |
|---|---|---|---|---|---|---|---|---|---|---|---|---|---|---|---|
| Ser | Thr | Gln | Pro | Leu | Leu | Tyr | Glu | Ala | Ala | Ser | Pro | Phe | Asn | Thr | Glu |
|  |  |  | 1175 |  |  |  | 1180 |  |  |  | 1185 |  |  |  |  |

| GCA | TTG | CTG | CAA | CCT | TCC | TTT | CCG | GCT | TCT | GAT | GTT | GAC | ACC | TTG | CTT | 3714 |
|---|---|---|---|---|---|---|---|---|---|---|---|---|---|---|---|---|
| Ala | Leu | Leu | Gln | Pro | Ser | Phe | Pro | Ala | Ser | Asp | Val | Asp | Thr | Leu | Leu |  |
|  | 1190 |  |  |  | 1195 |  |  |  |  | 1200 |  |  |  |  |  |  |

| AAA | ACT | GCC | CTT | CCC | TCT | GGG | CCT | CGT | GAT | CCA | GTG | CTG | ACT | GAA | ACC | 3762 |
|---|---|---|---|---|---|---|---|---|---|---|---|---|---|---|---|---|
| Lys | Thr | Ala | Leu | Pro | Ser | Gly | Pro | Arg | Asp | Pro | Val | Leu | Thr | Glu | Thr |  |
| 1205 |  |  |  | 1210 |  |  |  |  | 1215 |  |  |  |  |  |  |  |

| CCC | ATG | GTT | GAG | CAA | AGT | AGC | TCT | TCC | GTA | TCT | CTT | CCC | CTG | GCA | TCA | 3810 |
|---|---|---|---|---|---|---|---|---|---|---|---|---|---|---|---|---|
| Pro | Met | Val | Glu | Gln | Ser | Ser | Ser | Ser | Val | Ser | Leu | Pro | Leu | Ala | Ser |  |
| 1220 |  |  |  | 1225 |  |  |  | 1230 |  |  |  |  | 1235 |  |  |  |

| GAG | TCT | GCT | TCA | AGC | AAA | AGC | ACG | CTG | CAC | TTT | ACA | TCT | GTA | CCA | GTT | 3858 |
|---|---|---|---|---|---|---|---|---|---|---|---|---|---|---|---|---|
| Glu | Ser | Ala | Ser | Ser | Lys | Ser | Thr | Leu | His | Phe | Thr | Ser | Val | Pro | Val |  |
|  |  |  | 1240 |  |  |  |  | 1245 |  |  |  |  | 1250 |  |  |  |

| CTC | AAT | ATG | TCA | CCT | TCT | GAT | GTG | CAC | CCC | ACT | TCA | CTT | CAA | CGC | TTA | 3906 |
|---|---|---|---|---|---|---|---|---|---|---|---|---|---|---|---|---|
| Leu | Asn | Met | Ser | Pro | Ser | Asp | Val | His | Pro | Thr | Ser | Leu | Gln | Arg | Leu |  |
|  |  | 1255 |  |  |  |  | 1260 |  |  |  |  | 1265 |  |  |  |  |

| ACA | GTT | CCT | CAC | TCG | AGG | GAG | GAA | TAT | TTT | GAA | CAA | GGT | TTG | CTT | AAG | 3954 |
|---|---|---|---|---|---|---|---|---|---|---|---|---|---|---|---|---|
| Thr | Val | Pro | His | Ser | Arg | Glu | Glu | Tyr | Phe | Glu | Gln | Gly | Leu | Leu | Lys |  |
| 1270 |  |  |  |  | 1275 |  |  |  |  | 1280 |  |  |  |  |  |  |

| AGC | AAA | AGT | CCC | CAG | CAA | GTC | CTG | CCG | TCC | TTG | CAC | AGC | CAT | GAC | GAG | 4002 |
|---|---|---|---|---|---|---|---|---|---|---|---|---|---|---|---|---|
| Ser | Lys | Ser | Pro | Gln | Gln | Val | Leu | Pro | Ser | Leu | His | Ser | His | Asp | Glu |  |
| 1285 |  |  |  |  | 1290 |  |  |  |  | 1295 |  |  |  |  |  |  |

| TTT | TTC | CAA | ACT | GCA | CAT | CTG | GAC | ATT | AGC | CAG | GCC | TAC | CCT | CCA | AAA | 4050 |
|---|---|---|---|---|---|---|---|---|---|---|---|---|---|---|---|---|
| Phe | Phe | Gln | Thr | Ala | His | Leu | Asp | Ile | Ser | Gln | Ala | Tyr | Pro | Pro | Lys |  |
| 1300 |  |  |  |  | 1305 |  |  |  |  | 1310 |  |  |  |  | 1315 |  |

| GGA | AGG | CAT | GCA | TTT | GCT | ACT | CCT | ATT | TTA | TCA | ATC | AAT | GAA | CCA | CAA | 4098 |
|---|---|---|---|---|---|---|---|---|---|---|---|---|---|---|---|---|
| Gly | Arg | His | Ala | Phe | Ala | Thr | Pro | Ile | Leu | Ser | Ile | Asn | Glu | Pro | Gln |  |
|  |  |  |  | 1320 |  |  |  |  | 1325 |  |  |  |  | 1330 |  |  |

| AAT | ACA | CTT | ATA | AAC | AGG | CTT | GTG | TAT | TCT | GAG | GAC | ATT | TTC | ATG | CAC | 4146 |
|---|---|---|---|---|---|---|---|---|---|---|---|---|---|---|---|---|
| Asn | Thr | Leu | Ile | Asn | Arg | Leu | Val | Tyr | Ser | Glu | Asp | Ile | Phe | Met | His |  |
|  |  |  |  | 1335 |  |  |  |  | 1340 |  |  |  |  | 1345 |  |  |

| CCT | GAA | ATT | TCT | ATT | ACT | GAT | AAG | GCA | CTT | ACT | GGT | CTA | CCA | ACG | ACC | 4194 |
|---|---|---|---|---|---|---|---|---|---|---|---|---|---|---|---|---|
| Pro | Glu | Ile | Ser | Ile | Thr | Asp | Lys | Ala | Leu | Thr | Gly | Leu | Pro | Thr | Thr |  |
|  |  |  |  | 1350 |  |  |  |  | 1355 |  |  |  |  | 1360 |  |  |

| GTT | TCT | GAT | GTA | CTT | ATA | GCT | ACT | GAC | CAT | TCT | GTT | CCA | TTA | GGA | AGT | 4242 |
|---|---|---|---|---|---|---|---|---|---|---|---|---|---|---|---|---|
| Val | Ser | Asp | Val | Leu | Ile | Ala | Thr | Asp | His | Ser | Val | Pro | Leu | Gly | Ser |  |
|  |  |  | 1365 |  |  |  |  | 1370 |  |  |  |  | 1375 |  |  |  |

| GGG | CCC | ATT | TCC | ATG | ACA | ACT | GTT | TCT | CCC | AAC | AGA | GAT | GAT | TCT | GTG | 4290 |
|---|---|---|---|---|---|---|---|---|---|---|---|---|---|---|---|---|
| Gly | Pro | Ile | Ser | Met | Thr | Thr | Val | Ser | Pro | Asn | Arg | Asp | Asp | Ser | Val |  |
| 1380 |  |  |  |  | 1385 |  |  |  |  | 1390 |  |  |  |  | 1395 |  |

| ACC | ACA | ACC | AAG | TTG | CTT | CTT | CCT | TCT | AAA | GCT | ACT | TCT | AAG | CCG | ACT | 4338 |
|---|---|---|---|---|---|---|---|---|---|---|---|---|---|---|---|---|
| Thr | Thr | Thr | Lys | Leu | Leu | Leu | Pro | Ser | Lys | Ala | Thr | Ser | Lys | Pro | Thr |  |
|  |  |  |  | 1400 |  |  |  |  | 1405 |  |  |  |  | 1410 |  |  |

| CAT | AGT | GCC | AGA | TCT | GAT | GCC | GAT | TTA | GTA | GGA | GGT | GGT | GAA | GAT | GGT | 4386 |
|---|---|---|---|---|---|---|---|---|---|---|---|---|---|---|---|---|
| His | Ser | Ala | Arg | Ser | Asp | Ala | Asp | Leu | Val | Gly | Gly | Gly | Glu | Asp | Gly |  |
|  |  |  | 1415 |  |  |  |  | 1420 |  |  |  |  | 1425 |  |  |  |

| GAT | GAC | TAT | GAT | GAT | GAT | GAT | TAT | GAT | GAC | ATA | GAT | AGT | GAT | CGC | TTT | 4434 |
|---|---|---|---|---|---|---|---|---|---|---|---|---|---|---|---|---|
| Asp | Asp | Tyr | Asp | Asp | Asp | Asp | Tyr | Asp | Asp | Ile | Asp | Ser | Asp | Arg | Phe |  |
|  |  | 1430 |  |  |  |  | 1435 |  |  |  |  | 1440 |  |  |  |  |

| CCC | GTA | AAT | AAG | TGT | ATG | TCA | TGT | TCA | CCC | TAT | AGA | GAA | TCA | CAG | GAA | 4482 |
|---|---|---|---|---|---|---|---|---|---|---|---|---|---|---|---|---|
| Pro | Val | Asn | Lys | Cys | Met | Ser | Cys | Ser | Pro | Tyr | Arg | Glu | Ser | Gln | Glu |  |
|  | 1445 |  |  |  |  | 1450 |  |  |  |  | 1455 |  |  |  |  |  |

| AAG | GTA | ATG | AAT | GAC | TCG | GAC | ACC | CAA | GAA | AGC | AGT | CTT | GTG | GAT | CAG | 4530 |
|---|---|---|---|---|---|---|---|---|---|---|---|---|---|---|---|---|
| Lys | Val | Met | Asn | Asp | Ser | Asp | Thr | Gln | Glu | Ser | Ser | Leu | Val | Asp | Gln |  |
| 1460 |  |  |  |  | 1465 |  |  |  |  | 1470 |  |  |  |  | 1475 |  |

| AGT | GAC | CCA | ATT | TCA | CAT | TTG | CTC | TCT | GAG | AAT | ACC | GAA | GAA | GAA | AAT | 4578 |
|---|---|---|---|---|---|---|---|---|---|---|---|---|---|---|---|---|
| Ser | Asp | Pro | Ile | Ser | His | Leu | Leu | Ser | Glu | Asn | Thr | Glu | Glu | Glu | Asn |  |
|  |  |  |  | 1480 |  |  |  |  | 1485 |  |  |  |  | 1490 |  |  |

| GGA | GGC | ACG | GGT | GTA | ACT | AGG | GTG | GAT | AAA | AGT | CCT | GAT | AAG | TCA | CCA | 4626 |
|---|---|---|---|---|---|---|---|---|---|---|---|---|---|---|---|---|

| | | | | | | | | | | | | | | | | |
|---|---|---|---|---|---|---|---|---|---|---|---|---|---|---|---|---|
| Gly | Gly | Thr | Gly | Val | Thr | Arg | Val | Asp | Lys | Ser | Pro | Asp | Lys | Ser | Pro | |
| | | | 1495 | | | | | 1500 | | | | | 1505 | | | |

| | | | | | | | | | | | | | | | | |
|---|---|---|---|---|---|---|---|---|---|---|---|---|---|---|---|---|
| CCA | CCA | AGT | ATG | CTA | CCC | CAG | AAG | CAC | AAT | GAT | GGA | AGA | GAG | GAC | CGT | 4674 |
| Pro | Pro | Ser | Met | Leu | Pro | Gln | Lys | His | Asn | Asp | Gly | Arg | Glu | Asp | Arg | |
| | | | 1510 | | | | | 1515 | | | | | 1520 | | | |
| GAC | ATT | CAG | ATG | GGT | AGT | GCT | GTC | CTT | CCT | CAC | ACC | CCA | GGA | TCT | AAA | 4722 |
| Asp | Ile | Gln | Met | Gly | Ser | Ala | Val | Leu | Pro | His | Thr | Pro | Gly | Ser | Lys | |
| | | 1525 | | | | | 1530 | | | | | 1535 | | | | |
| GCA | TGG | GCA | GTT | TTG | ACA | AGT | GAT | GAA | GAG | AGT | GGG | TCA | GGG | CAA | GGC | 4770 |
| Ala | Trp | Ala | Val | Leu | Thr | Ser | Asp | Glu | Glu | Ser | Gly | Ser | Gly | Gln | Gly | |
| 1540 | | | | | 1545 | | | | | 1550 | | | | | 1555 | |
| ACC | TCA | GAT | AGC | CTT | AAT | GAT | AAT | GAG | ACT | TCC | ACA | GAT | TTC | AGT | TTC | 4818 |
| Thr | Ser | Asp | Ser | Leu | Asn | Asp | Asn | Glu | Thr | Ser | Thr | Asp | Phe | Ser | Phe | |
| | | | | 1560 | | | | | 1565 | | | | | 1570 | | |
| CCA | GAT | GTT | AAT | GAA | AAG | GAT | GCT | GAT | GGT | GTC | CTG | GAA | GCA | GAT | GAC | 4866 |
| Pro | Asp | Val | Asn | Glu | Lys | Asp | Ala | Asp | Gly | Val | Leu | Glu | Ala | Asp | Asp | |
| | | | | 1575 | | | | | 1580 | | | | | 1585 | | |
| ACA | GGC | ATA | GCT | CCG | GGA | TCT | CCA | CGG | TCC | TCC | ACA | CCA | TCT | GTT | ACT | 4914 |
| Thr | Gly | Ile | Ala | Pro | Gly | Ser | Pro | Arg | Ser | Ser | Thr | Pro | Ser | Val | Thr | |
| | | | 1590 | | | | | 1595 | | | | | 1600 | | | |
| AGT | GGG | CAT | TCA | GGA | GTA | TCC | AAC | AGT | TCA | GAG | GCA | GGT | TAGTTATGAG | | | 4963 |
| Ser | Gly | His | Ser | Gly | Val | Ser | Asn | Ser | Ser | Glu | Ala | Gly | | | | |
| | | 1605 | | | | | 1610 | | | | | 1615 | | | | |

| | | | | |
|---|---|---|---|---|
| CAAAGGGATA | GAACGAGATG | TGCTGATTTT | CTTGCTATGA | AAGTAAAAAT AGAAGAGTCA | 5023 |
| CGGAAGAAAA | GAATTCTGGT | CCACCAGCAG | ATCTTCACTT | TCTAATCAGA ACGTTCAATA | 5083 |
| CATTTATAGC | TCTTATAAAT | ATGGTTTTAC | TCATGATTTC | GAATGAATAT CCAACATATT | 5143 |
| TTGGTTATTG | ATTTTTATTA | TCTTCAAAAT | GCATTGTGTG | CTGTTACTAA TCCCTATTCC | 5203 |
| TATTGTGTGT | AGTATCAACT | ATGTATGCAT | AATACGCCAT | TAGAATATTA CAACGCAGTG | 5263 |
| TGCTGTGTTA | AGACAGTTTA | AATGTTCATA | CTTGTATTCT | GAAACAAGTT GTACACAAAC | 5323 |
| TCTATTGGAT | TTAAAATCTC | AGTAATATGC | TATAAGCACC | CATCCACCAA TGGTGGACAC | 5383 |
| TTCACATGTG | CACAACAGCT | TGGAGAGCTT | CTCAAAAGAA | CTACAGGGCT AAGATTTGAT | 5443 |
| AGCTAAGGAA | GGTTTTTATA | AACATCATAC | TGCTTTTAAA | CTATCCTTGA GCTTCTTTTT | 5503 |
| TGTTGCCTAA | AGAGGGCAGT | ATAAACCACC | AAAATACATT | CTACTTTGTG TTTGTTACAG | 5563 |
| TATTCCAACT | TACTAATCGA | CATGAATATG | CAGAAGATGC | ATAGGTATTG TATGACAAGA | 5623 |
| TGTAAAAGAA | AAAGCCTACA | GCCTTTTCTG | TAGAGATGCA | TTTCATTGTT AATATATTTT | 5683 |
| ATGCAAATGG | GTTTATTAGC | CAGATGTTTC | TTGGAGCAGA | CTGCAACCTA GAATACAGAT | 5743 |
| GTGTGCTTTA | AATGTCAATG | GTAACAAAAT | TCGAAATTCC | ATTAAGTGTT TAAAAAAAAA | 5803 |
| ACTAGGTGAT | TCCATTGAAT | TCACGGCAAG | AATTTTATAA | TTTGCTTTGA TTAAGTGATG | 5863 |
| AGGTTTTTTT | TTAATGCACA | AGGAAAGTAT | TTAAATCTTA | GCAAGTCAAA AGATAAGATA | 5923 |
| ATGTATAATG | TGACATTGGG | TAATAATTGC | ACAGAGCTTA | ATATTAAAAA TCCACAGTAT | 5983 |
| AGAGCCAATC | TCATTAAAAT | ATATATTCTC | TTTGTTATTT | TCATCATTCA CATTAGTTGT | 6043 |
| AAACTCTTTA | GTATGGCAGC | AATTAAGAGA | TTATATATTT | AGATAAGACA GTTTCTTTCT | 6103 |
| TTTCTGTATT | CTGACGTGAT | CTCCACTTAA | CGTTGAATTT | CAGCTTCAAT ATATGAACTG | 6163 |
| ATGTGTGAGA | AGGAGTAATG | AGTCCATGGG | TCACTGTAGT | CAGGAATGTT GTTACATATG | 6223 |
| TGAATTGTTA | TCTGTCCTCA | ATTATAGCAC | TTGTTTTTCT | TTCTATATTT TTAGATTTAT | 6283 |
| CTGAAAGGGA | AAGATCGTGA | ACATACTCTA | ATGGACAGAC | CATGCATATA CATATATCCC | 6343 |
| AAAGCACTAT | ATCTAGAATT | ATCGAAGAAA | GTTATTCTC | TTAGATGTAC TAATTAGATT | 6403 |
| TATTTAACTG | TTAAGAGTAA | GTTCCCCCAC | TAATGAAAAC | ACAGCAATAT GGATAAAACA | 6463 |

```
TCCATCTTCA GGAAATAATA CAGTTAATGA AGGGAGTAGG ATCAAATAGA ATTAGGGAAA      6523

ACAATTTTTA CCTGTTTTTA AAGCTGTATC TGTAAAACTA ATTCAAAGTC AGTCTTATCC      6583

AATTATTGAA TATTCCCTAG TCTGAAACTC ATCATTTATG GTACTTCTAA ATTGTAGAAA      6643

AACTGACATG ATGTTTCCTA ACTAATATA  AATAGGGCAA ATATAGATGA GAGTGAACAA      6703

AGACTGTAAG ATACTTGCTC TGGTTCACAT AAAGAGTCCA TCCAAAACTA ACCCTGGGAA      6763

TGTATTATTA GTGTCTGTCT CTTAGAACAT GCTTACAT                              6801
```

( 2 ) INFORMATION FOR SEQ ID NO:7:

( i ) SEQUENCE CHARACTERISTICS:
        ( A ) LENGTH: 1616 amino acids
        ( B ) TYPE: amino acid
        ( D ) TOPOLOGY: linear ( i i ) MOLECULE TYPE: protein ( x i ) SEQUENCE DESCRIPTION: SEQ ID NO:7:

```
Met Arg Ile Leu Gln Ser Phe Leu Ala Cys Val Gln Leu Leu Cys Val
 1               5                  10                  15

Cys Arg Leu Asp Trp Ala Tyr Gly Tyr Tyr Arg Gln Gln Arg Lys Leu
                20                  25                  30

Val Glu Glu Ile Gly Trp Ser Tyr Thr Gly Ala Leu Asn Gln Lys Asn
            35                  40                  45

Trp Gly Lys Lys Tyr Pro Ile Cys Asn Ser Pro Lys Gln Ser Pro Ile
        50                  55                  60

Asn Ile Asp Glu Asp Leu Thr Gln Val Asn Val Asn Leu Lys Lys Leu
65                  70                  75                  80

Lys Phe Gln Gly Trp Glu Lys Pro Ser Leu Glu Asn Thr Phe Ile His
                85                  90                  95

Asn Thr Gly Lys Thr Val Glu Ile Asn Leu Thr Asn Asp Tyr Tyr Leu
                100                 105                 110

Ser Gly Gly Leu Ser Glu Lys Val Phe Lys Ala Ser Lys Met Thr Phe
                115                 120                 125

His Trp Gly Lys Cys Asn Val Ser Ser Glu Gly Ser Glu His Ser Leu
    130                 135                 140

Glu Gly Gln Lys Phe Pro Leu Glu Met Gln Ile Tyr Cys Phe Asp Ala
145                 150                 155                 160

Asp Arg Phe Ser Ser Phe Glu Glu Thr Val Lys Gly Lys Gly Arg Leu
                165                 170                 175

Arg Ala Leu Ser Ile Leu Phe Glu Ile Gly Val Glu Glu Asn Leu Asp
                180                 185                 190

Tyr Lys Ala Ile Ile Asp Gly Thr Glu Ser Val Ser Arg Phe Gly Lys
                195                 200                 205

Gln Ala Ala Leu Asp Pro Phe Ile Leu Gln Asn Leu Leu Pro Asn Ser
    210                 215                 220

Thr Asp Lys Tyr Tyr Ile Tyr Asn Gly Ser Leu Thr Ser Pro Pro Cys
225                 230                 235                 240

Thr Asp Thr Val Glu Trp Ile Val Phe Lys Asp Thr Val Ser Ile Ser
                245                 250                 255

Glu Ser Gln Leu Ala Val Phe Cys Glu Val Leu Thr Met Gln Gln Ser
                260                 265                 270

Gly Tyr Val Met Leu Met Asp Tyr Leu Gln Asn Asn Phe Arg Glu Gln
                275                 280                 285

Gln Tyr Lys Phe Ser Arg Gln Val Phe Ser Ser Tyr Thr Gly Lys Glu
```

|     |     |     |     |     |     |     |     |     |     |     |     |     |     |     |
|-----|-----|-----|-----|-----|-----|-----|-----|-----|-----|-----|-----|-----|-----|-----|
|     |     | 290 |     |     |     | 295 |     |     |     | 300 |     |     |     |     |
| Glu | Ile | His | Glu | Ala | Val | Cys | Ser | Ser | Glu | Pro | Glu | Asn | Val | Gln | Ala |
| 305 |     |     |     |     | 310 |     |     |     | 315 |     |     |     |     | 320 |
| Asp | Pro | Glu | Asn | Tyr | Thr | Ser | Leu | Leu | Ile | Thr | Trp | Glu | Arg | Pro | Arg |
|     |     |     |     | 325 |     |     |     | 330 |     |     |     |     | 335 |     |
| Val | Val | Tyr | Asp | Thr | Met | Ile | Glu | Lys | Phe | Ala | Val | Leu | Tyr | Gln | Pro |
|     |     |     | 340 |     |     |     | 345 |     |     |     | 350 |     |     |     |
| Leu | Glu | Gly | Asn | Asp | Gln | Thr | Lys | His | Glu | Phe | Leu | Thr | Asp | Gly | Tyr |
|     |     | 355 |     |     |     | 360 |     |     |     | 365 |     |     |     |     |
| Gln | Asp | Leu | Gly | Ala | Ile | Leu | Asn | Asn | Leu | Ile | Pro | Asn | Met | Ser | Tyr |
|     | 370 |     |     |     | 375 |     |     |     | 380 |     |     |     |     |     |
| Val | Leu | Gln | Ile | Val | Ala | Ile | Cys | Ser | Asn | Gly | Leu | Tyr | Gly | Lys | Tyr |
| 385 |     |     |     | 390 |     |     |     | 395 |     |     |     |     |     | 400 |
| Ser | Asp | Gln | Leu | Ile | Val | Asp | Met | Pro | Thr | Glu | Asp | Ala | Glu | Leu | Asp |
|     |     |     | 405 |     |     |     | 410 |     |     |     | 415 |     |     |     |
| Leu | Phe | Pro | Glu | Leu | Ile | Gly | Thr | Glu | Glu | Ile | Ile | Lys | Glu | Glu | Asn |
|     |     | 420 |     |     |     | 425 |     |     |     | 430 |     |     |     |     |
| Tyr | Gly | Lys | Gly | Asn | Glu | Glu | Asp | Thr | Gly | Leu | Asn | Pro | Gly | Arg | Asp |
|     | 435 |     |     |     | 440 |     |     |     | 445 |     |     |     |     |     |
| Ser | Ala | Thr | Asn | Gln | Ile | Arg | Lys | Lys | Glu | Pro | Gln | Val | Ser | Thr | Thr |
| 450 |     |     |     | 455 |     |     |     | 460 |     |     |     |     |     |     |
| Thr | His | Tyr | Asn | His | Met | Gly | Thr | Lys | Tyr | Asn | Glu | Ala | Lys | Thr | Asn |
| 465 |     |     |     | 470 |     |     |     | 475 |     |     |     |     | 480 |     |
| Arg | Ser | Pro | Thr | Arg | Gly | Ser | Glu | Phe | Ser | Gly | Lys | Ser | Asp | Val | Leu |
|     |     |     | 485 |     |     |     | 490 |     |     |     | 495 |     |     |     |
| Asn | Thr | Ser | Leu | Asn | Pro | Thr | Ser | Gln | Gln | Val | Ala | Glu | Phe | Asn | Pro |
|     |     | 500 |     |     |     | 505 |     |     |     | 510 |     |     |     |     |
| Glu | Arg | Glu | Met | Ser | Leu | Pro | Ser | Gln | Ile | Gly | Thr | Asn | Leu | Pro | Pro |
|     | 515 |     |     |     | 520 |     |     |     | 525 |     |     |     |     |     |
| His | Ser | Val | Glu | Gly | Thr | Ser | Ala | Ser | Leu | Asn | Ser | Gly | Ser | Lys | Thr |
| 530 |     |     |     | 535 |     |     |     | 540 |     |     |     |     |     |     |
| Leu | Leu | Val | Phe | Pro | Gln | Met | Asn | Leu | Ser | Gly | Thr | Ala | Glu | Ser | Leu |
| 545 |     |     |     | 550 |     |     |     | 555 |     |     |     |     | 560 |     |
| Asn | Met | Val | Ser | Ile | Thr | Glu | Tyr | Lys | Glu | Val | Ser | Ala | Asp | Leu | Ser |
|     |     |     | 565 |     |     |     | 570 |     |     |     | 575 |     |     |     |
| Glu | Glu | Glu | Asn | Leu | Leu | Thr | Asp | Phe | Lys | Leu | Asp | Ser | Gly | Ala | Asp |
|     |     | 580 |     |     |     | 585 |     |     |     | 590 |     |     |     |     |
| Asp | Ser | Ser | Gly | Ser | Ser | Pro | Ala | Ser | Ser | Thr | Val | Pro | Phe | Ser | Thr |
|     | 595 |     |     |     | 600 |     |     |     | 605 |     |     |     |     |     |
| Asp | Asn | Leu | Ser | His | Gly | Tyr | Thr | Ser | Ser | Ser | Asp | Thr | Pro | Glu | Ala |
|     | 610 |     |     |     | 615 |     |     |     | 620 |     |     |     |     |     |
| Val | Thr | Tyr | Asp | Val | Leu | Arg | Pro | Glu | Ser | Thr | Arg | Asn | Ala | Leu | Glu |
| 625 |     |     |     | 630 |     |     |     | 635 |     |     |     |     | 640 |     |
| Asp | Ser | Ala | Pro | Ser | Gly | Ser | Glu | Glu | Ser | Leu | Lys | Asp | Pro | Ser | Leu |
|     |     |     | 645 |     |     |     | 650 |     |     |     | 655 |     |     |     |
| Glu | Gly | Ser | Val | Trp | Phe | Pro | Gly | Ser | Thr | Asp | Leu | Thr | Thr | Gln | Ser |
|     |     |     | 660 |     |     |     | 665 |     |     |     | 670 |     |     |     |
| Glu | Thr | Gly | Ser | Gly | Arg | Glu | Gly | Phe | Leu | Gln | Val | Asn | Ser | Thr | Asp |
|     |     | 675 |     |     |     | 680 |     |     |     | 685 |     |     |     |     |
| Phe | Gln | Val | Asp | Glu | Ser | Arg | Glu | Thr | Thr | Glu | Thr | Phe | Ser | Pro | Asp |
|     | 690 |     |     |     | 695 |     |     |     | 700 |     |     |     |     |     |
| Ala | Thr | Ala | Ser | Arg | Gly | Pro | Ser | Val | Thr | Asp | Met | Glu | Met | Pro | His |
| 705 |     |     |     | 710 |     |     |     | 715 |     |     |     |     | 720 |     |

```
Tyr  Ser  Thr  Phe  Ala  Tyr  Pro  Pro  Thr  Glu  Val  Thr  Ser  His  Ala  Phe
               725                 730                      735

Thr  Pro  Ser  Ser  Arg  Pro  Leu  Asp  Leu  Ala  Pro  Thr  Ser  Asn  Ile  Leu
               740                 745                      750

His  Ser  Gln  Thr  Thr  Gln  Pro  Val  Tyr  Asn  Gly  Glu  Thr  Pro  Leu  Gln
     755                           760                 765

Pro  Ser  Tyr  Ser  Ser  Glu  Val  Phe  Pro  Leu  Val  Thr  Pro  Leu  Leu  Leu
770                           775                      780

Asp  Asn  Gln  Thr  Leu  Asn  Thr  Thr  Pro  Ala  Ala  Ser  Ser  Ser  Asp  Ser
785                      790                 795                           800

Ala  Leu  His  Ala  Thr  Pro  Val  Phe  Pro  Ser  Val  Gly  Val  Ser  Phe  Asp
                    805                 810                           815

Ser  Ile  Leu  Ser  Ser  Tyr  Asp  Asp  Ala  Pro  Leu  Leu  Pro  Phe  Ser  Ser
               820                 825                      830

Ala  Ser  Phe  Ser  Ser  Asp  Leu  Phe  His  His  Leu  His  Thr  Val  Ser  Gln
          835                      840                 845

Thr  Leu  Pro  Gln  Val  Thr  Ser  Ala  Ala  Glu  Arg  Asp  Glu  Leu  Ser  Leu
     850                      855                 860

His  Ala  Ser  Leu  Leu  Val  Ala  Gly  Gly  Asp  Leu  Leu  Leu  Glu  Pro  Ser
865                      870                      875                      880

Leu  Val  Gln  Tyr  Ser  Asp  Val  Met  Ser  His  Gln  Val  Thr  Ile  His  Ala
                    885                 890                           895

Ala  Ser  Asp  Thr  Leu  Glu  Phe  Gly  Ser  Glu  Ser  Ala  Val  Leu  Tyr  Lys
               900                 905                      910

Thr  Ser  Met  Val  Ser  Gln  Ile  Glu  Ser  Pro  Ser  Ser  Asp  Val  Val  Met
          915                      920                 925

His  Ala  Tyr  Ser  Ser  Gly  Pro  Glu  Thr  Ser  Tyr  Ala  Ile  Glu  Gly  Ser
     930                      935                 940

His  His  Val  Leu  Thr  Val  Ser  Ser  Ser  Ala  Ile  Pro  Val  His  Asp
945                      950                      955                      960

Ser  Val  Gly  Val  Ala  Asp  Gln  Gly  Ser  Leu  Leu  Ile  Asn  Pro  Ser  His
                    965                 970                           975

Ile  Ser  Leu  Pro  Glu  Ser  Ser  Phe  Ile  Thr  Pro  Thr  Ala  Ser  Leu  Leu
               980                 985                      990

Gln  Leu  Pro  Pro  Ala  Leu  Ser  Gly  Asp  Gly  Glu  Trp  Ser  Gly  Ala  Ser
     995                      1000                1005

Ser  Asp  Ser  Glu  Leu  Leu  Leu  Pro  Asp  Thr  Asp  Gly  Leu  Arg  Thr  Leu
     1010                     1015                     1020

Asn  Met  Ser  Ser  Pro  Val  Ser  Val  Ala  Asp  Phe  Thr  Tyr  Thr  Thr  Ser
1025                     1030                     1035                     1040

Val  Ser  Gly  Asp  Asp  Ile  Lys  Pro  Leu  Ser  Lys  Gly  Glu  Met  Met  Tyr
                    1045                1050                          1055

Gly  Asn  Glu  Thr  Glu  Leu  Lys  Met  Ser  Ser  Phe  Ser  Asp  Met  Ala  Tyr
               1060                     1065                     1070

Pro  Ser  Lys  Ser  Thr  Val  Val  Pro  Lys  Met  Ser  Asp  Ile  Val  Asn  Lys
          1075                     1080                     1085

Trp  Ser  Glu  Ser  Leu  Lys  Glu  Thr  Ser  Val  Ser  Val  Ser  Ser  Ile  Asn
     1090                     1095                     1100

Ser  Val  Phe  Thr  Glu  Ser  Leu  Val  Tyr  Pro  Ile  Thr  Lys  Val  Phe  Asp
1105                          1110                     1115                1120

Gln  Glu  Ile  Ser  Arg  Val  Pro  Glu  Ile  Ile  Phe  Pro  Val  Lys  Pro  Thr
                    1125                     1130                     1135

His  Thr  Ala  Ser  Gln  Ala  Ser  Gly  Asp  Thr  Trp  Leu  Lys  Pro  Gly  Leu
               1140                     1145                     1150
```

```
Ser  Thr  Asn  Ser  Glu  Pro  Ala  Leu  Ser  Asp  Thr  Ala  Ser  Ser  Glu  Val
         1155                1160                1165

Ser  His  Pro  Ser  Thr  Gln  Pro  Leu  Leu  Tyr  Glu  Ala  Ala  Ser  Pro  Phe
         1170                1175                1180

Asn  Thr  Glu  Ala  Leu  Leu  Gln  Pro  Ser  Phe  Pro  Ala  Ser  Asp  Val  Asp
1185                1190                1195                               1200

Thr  Leu  Leu  Lys  Thr  Ala  Leu  Pro  Ser  Gly  Pro  Arg  Asp  Pro  Val  Leu
              1205                1210                1215

Thr  Glu  Thr  Pro  Met  Val  Glu  Gln  Ser  Ser  Ser  Val  Ser  Leu  Pro
              1220                1225                1230

Leu  Ala  Ser  Glu  Ser  Ala  Ser  Ser  Lys  Ser  Thr  Leu  His  Phe  Thr  Ser
              1235                1240                1245

Val  Pro  Val  Leu  Asn  Met  Ser  Pro  Ser  Asp  Val  His  Pro  Thr  Ser  Leu
         1250                1255                1260

Gln  Arg  Leu  Thr  Val  Pro  His  Ser  Arg  Glu  Glu  Tyr  Phe  Glu  Gln  Gly
1265                1270                1275                               1280

Leu  Leu  Lys  Ser  Lys  Ser  Pro  Gln  Gln  Val  Leu  Pro  Ser  Leu  His  Ser
              1285                1290                1295

His  Asp  Glu  Phe  Phe  Gln  Thr  Ala  His  Leu  Asp  Ile  Ser  Gln  Ala  Tyr
              1300                1305                1310

Pro  Pro  Lys  Gly  Arg  His  Ala  Phe  Ala  Thr  Pro  Ile  Leu  Ser  Ile  Asn
              1315                1320                1325

Glu  Pro  Gln  Asn  Thr  Leu  Ile  Asn  Arg  Leu  Val  Tyr  Ser  Glu  Asp  Ile
         1330                1335                1340

Phe  Met  His  Pro  Glu  Ile  Ser  Ile  Thr  Asp  Lys  Ala  Leu  Thr  Gly  Leu
1345                1350                1355                               1360

Pro  Thr  Thr  Val  Ser  Asp  Val  Leu  Ile  Ala  Thr  Asp  His  Ser  Val  Pro
              1365                1370                1375

Leu  Gly  Ser  Gly  Pro  Ile  Ser  Met  Thr  Thr  Val  Ser  Pro  Asn  Arg  Asp
              1380                1385                1390

Asp  Ser  Val  Thr  Thr  Thr  Lys  Leu  Leu  Leu  Pro  Ser  Lys  Ala  Thr  Ser
              1395                1400                1405

Lys  Pro  Thr  His  Ser  Ala  Arg  Ser  Asp  Ala  Asp  Leu  Val  Gly  Gly  Gly
         1410                1415                1420

Glu  Asp  Gly  Asp  Asp  Tyr  Asp  Asp  Asp  Tyr  Asp  Asp  Ile  Asp  Ser
1425                1430                1435                               1440

Asp  Arg  Phe  Pro  Val  Asn  Lys  Cys  Met  Ser  Cys  Ser  Pro  Tyr  Arg  Glu
              1445                1450                1455

Ser  Gln  Glu  Lys  Val  Met  Asn  Asp  Ser  Asp  Thr  Gln  Glu  Ser  Ser  Leu
              1460                1465                1470

Val  Asp  Gln  Ser  Asp  Pro  Ile  Ser  His  Leu  Leu  Ser  Glu  Asn  Thr  Glu
              1475                1480                1485

Glu  Glu  Asn  Gly  Gly  Thr  Gly  Val  Thr  Arg  Val  Asp  Lys  Ser  Pro  Asp
              1490                1495                1500

Lys  Ser  Pro  Pro  Pro  Ser  Met  Leu  Pro  Gln  Lys  His  Asn  Asp  Gly  Arg
1505                1510                1515                               1520

Glu  Asp  Arg  Asp  Ile  Gln  Met  Gly  Ser  Ala  Val  Leu  Pro  His  Thr  Pro
              1525                1530                1535

Gly  Ser  Lys  Ala  Trp  Ala  Val  Leu  Thr  Ser  Asp  Glu  Glu  Ser  Gly  Ser
              1540                1545                1550

Gly  Gln  Gly  Thr  Ser  Asp  Ser  Leu  Asn  Asp  Asn  Glu  Thr  Ser  Thr  Asp
              1555                1560                1565

Phe  Ser  Phe  Pro  Asp  Val  Asn  Glu  Lys  Asp  Ala  Asp  Gly  Val  Leu  Glu
```

```
              1570                    1575                    1580
         Ala  Asp  Asp  Thr  Gly  Ile  Ala  Pro  Gly  Ser  Pro  Arg  Ser  Ser  Thr  Pro
         1585                    1590                    1595                    1600
         Ser  Val  Thr  Ser  Gly  His  Ser  Gly  Val  Ser  Asn  Ser  Ser  Glu  Ala  Gly
                             1605                    1610                    1615
```

( 2 ) INFORMATION FOR SEQ ID NO:8:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:8:

```
CCCTCGAGGA AGGCATGTAT TTGC                                                       24
```

( 2 ) INFORMATION FOR SEQ ID NO:9:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:9:

```
GCCTCTAGAT TCACCACCAC CCACTAAACC                                                 30
```

( 2 ) INFORMATION FOR SEQ ID NO:10:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( i x ) FEATURE:
        ( A ) NAME/KEY: misc_feature
        ( B ) LOCATION: one-of(33, 36)
        ( D ) OTHER INFORMATION: ote="N is inosine"

( x i ) SEQUENCE DESCRIPTION: SEQ ID NO:10:

```
CGAATTCTCG AGAARTGYGA YCARTAY-
TGG CCNGCNGA Y G                                                                 40
```

( 2 ) INFORMATION FOR SEQ ID NO:11:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:11:

```
GCTCTAGAAG CTTGTAGTCT GTGCCTTCCC CACTCAGG                                        38
```

( 2 ) INFORMATION FOR SEQ ID NO:12:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:12:

```
GCAATTCTCG AGCCTGTGGA AAGATCAAGG GTTGGC                                          36
```

( 2 ) INFORMATION FOR SEQ ID NO:13:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:13:

GCAATTAAGC TTATGCTCAT CATGAACAAT CATAGG                                        36

( 2 ) INFORMATION FOR SEQ ID NO:14:

( i ) SEQUENCE CHARACTERISTICS:
        ( A ) LENGTH: 34 base pairs
        ( B ) TYPE: nucleic acid
        ( C ) STRANDEDNESS: single
        ( D ) TOPOLOGY: linear ( i x ) FEATURE:
        ( A ) NAME/KEY: misc_feature
        ( B ) LOCATION: one-of(16, 19, 28, 31)
        ( D ) OTHER INFORMATION: ote="N is inosine"

( x i ) SEQUENCE DESCRIPTION: SEQ ID NO:14:

CCGCGGATCC AAR Y TNGTNG ARGARATNGG NTGG                                     34

( 2 ) INFORMATION FOR SEQ ID NO:15:

( i ) SEQUENCE CHARACTERISTICS:
        ( A ) LENGTH: 37 base pairs
        ( B ) TYPE: nucleic acid
        ( C ) STRANDEDNESS: single
        ( D ) TOPOLOGY: linear ( i x ) FEATURE:
        ( A ) NAME/KEY: misc_feature
        ( B ) LOCATION: 23
        ( D ) OTHER INFORMATION: ote="N is inosine"

( x i ) SEQUENCE DESCRIPTION: SEQ ID NO:15:

GCTTAAGCTT RTA Y TG Y TG Y TCNCK-
RAART TRTT Y TG                                                          37

( 2 ) INFORMATION FOR SEQ ID NO:16:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:16:

TCTCACCAAT GACTACTATC TC                                                      22

( 2 ) INFORMATION FOR SEQ ID NO:17:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:17:

AGTACTTGTC AGTGGAGTTT GG                                                      22

( 2 ) INFORMATION FOR SEQ ID NO:18:

( i ) SEQUENCE CHARACTERISTICS:
        ( A ) LENGTH: 7 amino acids

```
        ( B ) TYPE: amino acid
        ( C ) STRANDEDNESS: single
        ( D ) TOPOLOGY: linear ( x i ) SEQUENCE DESCRIPTION: SEQ ID NO:18:

Asp Asp Ser Ser Gly Ser Ser
1               5

( 2 ) INFORMATION FOR SEQ ID NO:19:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( x i ) SEQUENCE DESCRIPTION: SEQ ID NO:19:

Asp Gly Glu Trp Ser Gly Ala Gly
1               5

( 2 ) INFORMATION FOR SEQ ID NO:20:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( x i ) SEQUENCE DESCRIPTION: SEQ ID NO:20:

Asp Glu Glu Ser Gly Ser Gly Gln Gly
1               5

( 2 ) INFORMATION FOR SEQ ID NO:21:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( x i ) SEQUENCE DESCRIPTION: SEQ ID NO:21:

Glu Asp Ser Ala Pro Ser Gly Ser Glu Glu
1               5                  10
```

PHOSPHACAN: A CHONDROITIN SULFATE PROTEOGLYCAN OF BRAIN THAT INTERACTS WITH NEURONS AND NEURAL CELL ADHESION MOLECULES

This invention was funded in part by research grants NS-09348, NS-13876 and MH-00129 from the National Institutes of Health, which provides to the United States Government certain rights in this invention.

BACKGROUND OF THE INVENTION

1. Field of the Invention

The present invention in the field of neuroscience and medicine relates to novel eukaryotic phosphacan proteoglycan molecules, and functional derivatives thereof, as well as nucleic acid molecules encoding the protein backbone of the proteoglycan. These compositions are useful for providing soluble, biologically active phosphacan molecule or derivatives which are useful in inhibiting or promoting neural cell adhesion and related activities important to neuronal development and regeneration.

2. Description of the Background Art

Cell Adhesion Molecules and Ng-CAM

Cell-cell adhesion is a primary process that is critical for embryonic development and for pattern formation in the nervous system (Edelman, G. M. et al., 1990, *MORPHOREGULATORY MOLECULES*, John Wiley & Sons, New York). The ability of neurons to organize into specific patterns depends on their interactions with other neurons, with glia, and with the extracellular environment (Jacobson, M., 1991, *DEVELOPMENTAL NEUROBIOLOGY*, 3rd Edition, Plenum Press, New York). Many of these interactions between neural cells are mediated by cell adhesion molecules (CAMs) (Edelman, G. M., 1983, *Science* 219:450-457) which fall primarily into two different families. Members of the immunoglobulin superfamily (Edelman, G. M., 1987, *Immun. Rev.* 100:11-45) contain immunoglobulin domains and fibronectin type III repeats and have calcium-independent binding, while members of the cadherin family share distinct repeated domains and have calcium-dependent binding (Takeichi, M., 1988, *Development* 102:639-655).

CAMs such as the neuron-glia CAM, Ng-CAM (Grumet, M. et al., 1984, *J Cell Biol* 98:1746-1756) mediate cell-cell interactions and are expressed early during development in spatially and temporally restricted patterns (Edelman, G. M., 1988, *Biochemistry* 27:3533-3543; Jessell, T. M., 1988, *Cell* 1:3-13). Certain CAMs are transmembrane proteins which may participate in signal transmission between cells to modulate cell behavior and differentiation (Edelman G. M., 1976, *Science* 192:218-226; Schuch, U. et al., 1989, *Neuron* 3:13-20; Bixby, J. L., 1989, *Neuron* 3:287-297).

Ng-CAM is a large neuronal CAM of around 200 kDa that can mediate neuron-neuron and neuron-gila adhesion, and has been implicated in neuronal migration and the formation of nerve bundles. The biochemistry and biology of Ng-CAM is reviewed in Grumet, M., 1992, *J. Neurosci. Res.* 31:1-13, which is hereby incorporated by reference in its entirety. Ng-CAM binds homophilically (to itself) and heterophilically to several cell surface proteins. Ng-CAM is structurally related to human protein L1 (Reid, R. A. et al., 1992, *J. Mol. Neurosci.* 3:127-135), and binds to mammalian L1 (Grumet, M. et al., 1986, *J. Cell Biol.* 106:487-503; Lemmon, V. et al., 1989, *Neuron* 2:1597-1603). Purified Ng-CAM presented as a substrate for neurons in culture can promote neuritic fiber extension of about 100 μm in several hours.

The binding of certain CAMs including L1 to neurons generates signals such as an increase in intracellular calcium that have been associated with promotion of neurite growth (Schuch et al., supra; Williams, E. J. et al., 1992, *J. Cell Biol.* 119:883-892). Any molecules which bind to and inhibit or enhance their function may have a significant impact on axonal growth during development or regeneration following injury to the nervous system (Daniloff, J. K. et al., 1986b, *J. Cell. Biol.* 103:929-945)).

Chondroitin Sulfate Proteoglycans

Chondroitin sulfate proteoglycans are involved in modulating cell interactions in developing nervous tissue (Hoffman, S. et al., 1988 *J. Cell Biol.* 106:519-532; Crossin, K. L. et al., 1989 *Dev. Biol.* 136:381-392; Perris, R. et al. 1990 *Dev. Biol.* 137:1-12; Margolis, R. K. et al., 1991 *J. Cell Sci.* 99:237-246; Perris, R. et al., 1991 *Development* 111:583-599; Snow, D. M. et al., 1991 *Development* 113:1473-1485; Brittis, P. A. et al., 1992, *Science* 255:733-736). Such proteoglycans also serve as components of astroglial axon barriers (Snow, D. M. et al., 1990 *Dev. Biol.* 138:359-376; Snow, D. M. et al. 1990 *Exp. Neurol.* 109:111-130; McKeon, R. J. et al., 1991 *J. Neurosci.* 11:3398-3411; Oakley, R. A. et al., 1991 *Dev. Biol.* 147:187-206).

The present inventors and their colleagues have recently shown that two chondroitin sulfate proteoglycans from brain, neurocan and 3F8 (now termed "phosphacan", and the subject of the present invention) (Rauch, U. et al., 1991, *J. Biol. Chem.* 266:14785-14801) bind to Ng-CAM with high affinity and inhibit Ng-CAM function (Grumet, M. et al., 1993, *J. Cell. Biol* 120:815-824; Friedlander, D. R. et al., 1993, *J. Neurosci.* 19:626a). These proteoglycans may therefore inhibit nerve regrowth and neuronal cell division, thus acting as repulsive molecules which modulate cell-cell and cell-matrix interactions by providing a mechanism for diminishing adhesive forces, thereby permitting cell rounding, division, differentiation, and cell movement in developing brain. A distinct need therefore exists in the art for information on the primary structure or these proteoglycan molecules, as well as a more detailed functional understanding of the roles of their specific protein and carbohydrate domains.

The 3F8 proteoglycan was so named because it was isolated from a PBS extract of rat brain by immunoaffinity chromatography with the 3F8 monoclonal antibody (mAb). This proteoglycan was found to be developmentally regulated with respect to its sulfation, carbohydrate composition and oligosaccharide structure, and immunocytochemical localization in the CNS (Rauch, U. et al. (1991) *J. Biol. Chem.* 266:14785-14801). A second chondroitin/keratan sulfate proteoglycan, designated 3H1, was also isolated from rat brain using mAb 3H1 specific for the keratan sulfate chains (Rauch et al., supra).

The 3F8 proteoglycan, as well neurocan, inhibited (a) neurite outgrowth and (b) binding of neurons to Ng-CAM when mixtures of these proteins were adsorbed to polystyrene dishes. Direct binding of neurons to the proteoglycan core glycoproteins was demonstrated using an assay in which cell-substrate contact was initiated by centrifugation (Grumet et al., supra; Milev et al., (1993) *Glycobiology* 3:535; Milev, P. et al., (1993) *J. Neurochem.* 61 (*Suppl.*):S110C).

Citation of the above documents is not intended as an admission that any of the foregoing is pertinent prior art. All statements as to the date or representation as to the contents

SUMMARY OF THE INVENTION

The present inventors have now identified cDNA clones encoding a chondroitin sulfate proteoglycan of rat brain (previously designated 3F8 and now named phosphacan) which binds to neurons and neural cell adhesion molecules. 3F8 and neurocan, another chondroitin sulfate proteoglycan of brain whose primary structure has recently been described (Rauch, U. et al., (1992) *J. Biol. Chem.* 267:19536–19547), interact with neurons and the neural cell adhesion molecules, Ng-CAM and N-CAM (Grumet, M. et al., (1993) *J. Cell Biol.* 120:815–824). The brain proteoglycans bind with high affinity ($K_d$ of approximately 0.5 nM) to Ng-CAM and N-CAM but not to other cell surface and extracellular matrix proteins such as laminin, fibronectin, several collagens, or receptors for epidermal growth factor (EGF) or fibroblast growth factor (FGF), or the myelin associated glycoprotein (Milev, P. et al., (1993) *Glycobiology* 3:535).

A sequence of 1616 amino acids deduced from a 4.8 kb open reading frame contains the N-terminal amino acid sequence of the 3F8 core glycoprotein as well as four internal CNBr, tryptic, and endo Lys-C peptide sequences from the proteoglycan. The deduced amino acid sequence, beginning with a 24 amino acid signal peptide, reveals an N-terminal domain of 255 amino acids homologous to carbonic anhydrases.

The entire amino acid sequence deduced from the cDNA clones of the present invention has a degree of sequence homology (76% identity) to the extracellular portion of a human receptor-type protein tyrosine phosphatase (RPTPζ/β), leading the present inventors to suggest that the proteoglycan may represent an mRNA splicing variant of the larger transmembrane protein.

Northern analysis demonstrated that a probe to the N-terminal carbonic anhydrase domain of the proteoglycan hybridizes with rat brain mRNA of 9.5 kb, 8.4 kb, and 6.4 kb. In contrast, probes to the phosphatase domains of the RPTP hybridize with only the 9.5 and 6.4 kb message (which corresponds to a previously identified variant in which half of the extracellular domain is deleted).

The 30 N-terminal amino acids of the 3H1 chondroitin/keratan sulfate proteoglycan of brain are identical to those of the 3F8 proteoglycan, and six internal tryptic peptide sequences also matched those found in sequenced peptides of the 3F8 proteoglycan and/or amino acid sequences deduced from the cDNA clones.

The present inventors therefore concluded that the 3H1 chondroitin/keratan sulfate proteoglycan and the 3F8 chondroitin sulfate proteoglycan represent glycosylation and possible extracellular splicing variants of a receptor-type protein tyrosine phosphatase.

These proteoglycans are hypothesized to modulate cell interactions and other developmental processes in nervous tissue through heterophilic binding to cell surface and extracellular matrix molecules, and by competition with ligands of the transmembrane phosphatase.

The present invention is directed to an isolated phosphacan proteoglycan molecule or a functional derivative thereof lacking tyrosine phosphatase activity, wherein, when the molecule is one which naturally occurs, the molecule is substantially free of other proteins or proteoglycans with which it is natively associated.

The above phosphacan molecule is preferably a mammalian phosphacan, from a mammal selected from murine, bovine, ovine, human, rat, porcine, equine, canine, feline or caprine.

Also provided is a phosphacan proteoglycan molecule as above having the amino acid sequence SEQ ID NO:7, or a functional derivative thereof.

The above proteoglycan molecule is preferably one which binds to a neuron or to a cell adhesion molecule, preferably N-CAM or Ng-CAM. Also provided is a method for identifying a compound that binds to the above proteoglycan molecule, comprising
(a) exposing the compound to the proteoglycan molecule for a time sufficient to allow binding of the compound to the proteoglycan molecule;
(b) removing any unbound compound; and
(c) detecting the presence of the compound bound to the proteoglycan molecule.

The present invention is also directed to a method for isolating molecules that bind to the above proteoglycan molecule from a mixture, comprising the steps of:
(a) exposing the mixture to the proteoglycan molecule for a time sufficient to allow binding of any of the molecules to the proteoglycan molecule;
(b) removing any unbound molecules; and
(c) eluting the molecules bound to the proteoglycan molecule to thereby obtain isolated molecules, capable of binding the proteoglycan.

The present invention also provides a nucleic acid molecule encoding the protein portion of a phosphacan proteoglycan molecule or functional derivative as described above, wherein, when the protein or functional derivative is one which naturally occurs, the nucleic acid molecule is substantially free of nucleotide sequences encoding proteins with which the protein or functional derivative is natively associated.

The nucleic acid molecule may be a cDNA molecule or a genomic DNA molecule. The nucleic acid molecule preferably is a DNA molecule, having the nucleotide sequence SEQ ID:NO. 6.

The nucleic acid molecule may be an expression vehicle, such as a plasmid.

Also provided is a prokaryotic host or eukaryotic host transformed or transfected with the above expression vehicle.

The present invention is further directed to a process for preparing a phosphacan proteoglycan molecule as above, or a functional derivative thereof, the process comprising:
(a) culturing a host, either prokaryote or eukaryote, capable of expressing the proteoglycan or functional derivative under culturing conditions,
(b) expressing the proteoglycan or functional derivative; and
(c) recovering the proteoglycan or functional derivative from the culture.

Also provided is an antibody, polyclonal or monoclonal, specific for the above phosphacan proteoglycan molecule 1.

The present invention provides a method for detecting the presence of a nucleic acid molecule as described above, or a mutant or variant thereof, in a subject, comprising:
(a) contacting a cell or a nucleic acid-containing extract thereof from the subject with an oligonucleotide probe encoding at least a portion of the normal or the mutant or variant phosphacan proteoglycan under hybridizing conditions; and
(b) measuring the hybridization of the probe to the nucleic acid of the cell,
thereby detecting the presence of the nucleic acid sequence. Before step (b), the method may additionally comprise the step (c) selectively amplifying the amount of DNA of the cell encoding the phosphacan proteoglycan.

The present invention is also directed to a method for detecting in a cell or on the surface of a cell the presence of a phosphacan proteoglycan, or measuring the quantity of the phosphacan proteoglycan, comprising:

(a) contacting the cell or an extract thereof with an antibody as described above; and (b) detecting the binding of the antibody to the cell or extract thereof, or measuring the quantity of antibody bound, thereby determining the presence or measuring the quantity of the phosphacan proteoglycan.

In another embodiment, the present invention is directed to a pharmaceutical composition useful for nerve regeneration, comprising:

(a) a phosphacan proteoglycan molecule or a functional derivative thereof, or a pharmaceutically acceptable ester, ether, sulfate, carbonate, glucuronide or salt of phosphacan or of the functional derivative, in an amount effective for promoting nerve regeneration; and (b) a pharmaceutically acceptable carrier.

The above pharmaceutical may further comprise at least one other agent useful in promoting nerve regeneration.

The pharmaceutical compositions of the present invention may be provided in soluble form or adsorbed to a solid phase such as nitrocellulose from which they are slowly released, or from a depot from which they are slowly released.

In another embodiment, the compositions of the present invention may be used to inhibit nerve cell interactions that occur through the binding of cell-adhesion molecules to which the phosphacan or functional derivative can bind.

BRIEF DESCRIPTION OF THE DRAWINGS

FIG. 1 shows the N-terminal amino acid sequences (shown in single letter code in the Figure and in three letter code in SEQUENCE LISTING) of the 3F8 and 3H1 proteoglycan core proteins (SEQ ID NO:1), and of internal peptides obtained by CNBr (SEQ ID NO:2), trypsin (SEQ ID NO:3; SEQ ID NO:4), or endoproteinase Lys-C (SEQ ID NO:5). Underlined sections of the peptide sequences indicate regions used for the design of oligonucleotide primers, and the position of the internal peptides in the sequence shown in FIG. 2 is given in parenthesis.

FIG. 2 (comprising six pages) shows the nucleotide sequence [SEQ ID NO:6] and deduced amino acid sequence (shown in single letter code in the Figure and in three letter code in SEQUENCE LISTING) [SEQ ID NO:7] from 3FS/3H1 proteoglycan core protein cDNA. The contiguous cDNA sequence determined from overlapping clones is shown, together with the translation of a 4.8 kb open reading frame. Peptides from which 3F8 proteoglycan amino acid sequence data were obtained are shown in bold, and amino acid and nucleotide sequences used for the design of oligonucleotide primers for enzymatic amplification reactions are boxed or underlined. The clones used for sequencing are shown at the bottom of page 6 of FIG. 2, with the bold lines representing coding sequence.

DESCRIPTION OF THE PREFERRED EMBODIMENTS

Figure 3:
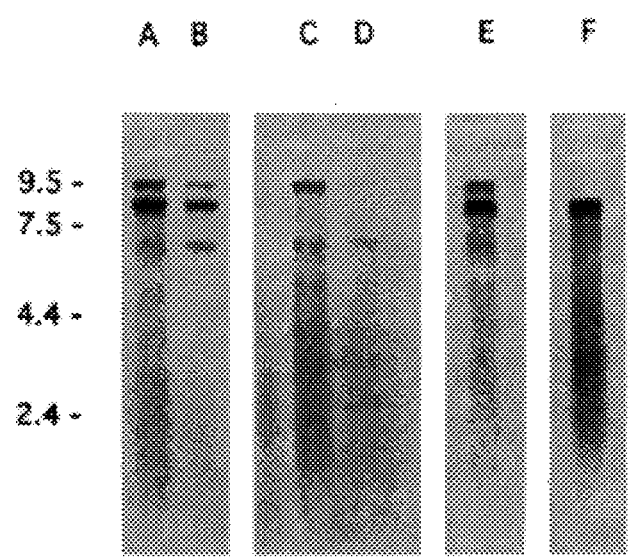
FIG. 3 shows a Northern blot of 4 μg of mRNA from 4-day old (lanes A, C, E and F) and adult rat brain (lanes B and D) electrophoresed on a 1% agarose gel containing 6% formaldehyde. Blots were probed with digoxigenin-labeled RNA transcripts corresponding to the N-terminal carbonic anhydrase domain (lanes A, B and E), to the cytoplasmic second phosphatase domain of the membrane tyrosine phosphatase PTPζ/RPTPβ (lanes C and D), and to an EcoRI fragment from the 3'-untranslated region of the extracellular form (lane F). The blot was stained with alkaline phosphatase-labeled anti-digoxigenin antibodies. Positions of RNA molecular size markers are indicated at the left.

The present inventors have discovered a novel phosphacan proteoglycan molecule which may be provided as an isolated naturally occurring molecule, or as a functional derivative thereof, for example, a fragment or variant. Also provided are compositions comprising a phosphacan proteoglycan as well as methods of making and using such molecules.

Phosphacan has the ability to bind to neural cell adhesion molecules such as Ng-CAM and N-CAM. Therefore, phosphacan or functional derivatives thereof can be used to competitively inhibit such CAM binding, and disrupt the biological processes which depend on CAM binding, or promote the processes which are inhibited by CAM binding.

In addition, because of the similarity of phosphacan to the RPTPβ extracellular receptor domain, phosphacan or functional derivatives thereof can be used as false receptors to bind to natural ligands to the receptor portion of RPTPβ. In this way, the compositions of the present invention can inhibit signal transduction and activation of tyrosine phosphatase enzymes, and interfere with the biological processes dependent on phosphatase activity.

Thus the present invention is directed to methods for inhibiting cell interactions mediated by CAMs, thereby promoting cell deadhesion, migration, mobility, differentiation and neuronal regeneration in the central nervous system.

PROTEINS, PEPTIDES AND THEIR FUNCTIONAL DERIVATIVES

It will be understood that the phosphacan proteoglycan molecule useful in the methods and compositions of the present invention can be biochemically purified from a cell or tissue source, preferably from postnatal brain. Methods for purifying phosphacan are well-known in the art and are described herein. See, also Rauch et al., 1991, supra, which reference is hereby incorporated by reference in its entirety.

Alternatively, DNA encoding the amino acid portion of phosphacan can be isolated or synthesized and used to synthesize the polypeptide (or proteoglycan) substantially free of other proteins or proteoglycans of mammalian origin in a prokaryotic host or in a eukaryotic host, if desired. Alternatively, methods are well known for the synthesis of polypeptides of desired sequence on solid phase supports and their subsequent separation from the support.

Functional Derivatives

In a further embodiment, the invention provides "functional derivatives" of phosphacan. By "functional derivative" is meant a "fragment," "variant," "analog," or "chemical derivative" of phosphacan. A functional derivative retains at least a portion of the function of phosphacan such as the activity of binding Ng-CAM, or binding to an anti-phosphacan antibody, which permits its utility in accordance with the present invention.

A "fragment" of phosphacan refers to any subset of the molecule, that is, having a shorter peptide backbone.

A "variant" of phosphacan refers to a molecule substantially similar to either the entire proteoglycan or a fragment thereof. Variant peptides may be conveniently prepared by direct chemical synthesis of the variant peptide, using methods well-known in the art.

Alternatively, amino acid sequence variants of the protein or peptide portion of the phosphacan molecule can be prepared by mutations in the DNA which encodes the synthesized peptide. Such variants include, for example, deletions from, or insertions or substitutions of, residues within the amino acid sequence. Any combination of deletion, insertion, and substitution may also be made to arrive at the final construct, provided that the final construct possesses the desired functional activity. Obviously, the mutations that will be made in the DNA encoding the variant peptide must not alter the reading frame and preferably will not create complementary regions that could produce secondary mRNA structure (see European Patent Publication No. EP 75,444).

At the genetic level, these variants ordinarily are prepared by site-directed mutagenesis (see, for example, Adelman et al. 1983, *DNA* 2:183) of nucleotides in the DNA encoding the phosphacan protein or a peptide fragment thereof, thereby producing DNA encoding the variant, and thereafter expressing the DNA in recombinant cell culture (see below). The variants typically exhibit the same qualitative biological activity as the nonvariant peptide.

A preferred group of variants of phosphacan are those in which at least one amino acid residue in the protein or in a peptide fragment thereof, and preferably, only one, has been removed and a different residue inserted in its place. For a detailed description of protein chemistry and structure, see Schulz, G. E. et al., *PRINCIPLES OF PROTEIN STRUCTURE*, Springer-Verlag, New York, 1978, and Creighton, T. E., *PROTEINS: STRUCTURE AND MOLECULAR PROPERTIES*, W. H. Freeman & Co., San Francisco, 1983, which are hereby incorporated by reference. The types of substitutions which may be made in the protein or peptide molecule of the present invention may be based on analysis of the frequencies of amino acid changes between a homologous protein of different species, such as those presented in Table 1-2 of Schulz et al. (supra) and FIG. 3–9 of Creighton (supra). Base on such an analysis, conservative substitutions are defined herein as exchanges within one of the following five groups:

1. Small aliphatic, nonpolar or slightly polar residues: Ala, Ser, Thr (Pro, Gly);
2. Polar, negatively charged residues and their amides: Asp, Asn, Glu, Gln;
3. Polar, positively charged residues: His, Arg, Lys;
4. Large aliphatic, nonpolar residues: Met, Leu, Ile, Val (Cys); and
5. Large aromatic residues: Phe, Tyr, Trp.

The three amino acid residues in parentheses above have special roles in protein architecture. Gly is the only residue lacking any side chain and thus imparts flexibility to the chain. Pro, because of its unusual geometry, tightly constrains the chain. Cys can participate in disulfide bond formation which is important in protein folding. Note the Schulz et al. would merge Groups 1 and 2, above. Note also that Tyr, because of its hydrogen bonding potential, has some kinship with Ser, Thr, etc.

Preferably, the substituted amino acid is not one to which the glycan moieties and chondroitin sulfate moieties are bound.

Substantial changes in functional or immunological properties of phosphacan are made by selecting substitutions that are less conservative, such as between, rather than within, the above five amino acid groups, above, which will differ more significantly in their effect on maintaining (a) the structure of the peptide backbone in the area of the substitution, for example, as a sheet or helical conformation, (b) the charge or hydrophobicity of the molecule at the target site, or (c) the bulk of the side chain. Examples of such substitutions are (a) substitution of gly and/or pro by another amino acid or deletion or insertion of gly or pro; (b) substitution of a hydrophilic residue, such as ser or thr, for (or by) a hydrophobic residue, such as leu, ile, phe, val or ala; (c) substitution of a cys residue for (or by) any other residue; (d) substitution of a residue having an electropositive side chain, such as lys, arg or his, for (or by) a residue having an electronegative charge, such as glu or asp; or (e) substitution of a residue having a bulky side chain, such as phe, for (or by) a residue not having such a side chain, such as gly.

Preferred deletions and insertions, and substitutions, according to the present invention, are those which do not produce radical changes in the characteristics of the protein or peptide portion of the proteoglycan molecule. However, when it is difficult to predict the exact effect of the substitution, deletion, or insertion in advance of doing so, one skilled in the art will appreciate that the effect will be evaluated by routine screening assays which are described in more detail below. For example, a change in the immunological character of the proteoglycan, such as binding to a given antibody, is measured by a competitive type immunoassay. Biological activity is screened in an appropriate binding assay or bioassay, as described herein, such as those which assess direct binding of neurons to the proteoglycan core glycoproteins (Grumet et al., supra; Milev et al., supra).

An "analog" of phosphacan refers to a non-natural molecule substantially similar to either the entire phosphacan molecule or a fragment thereof.

A "chemical derivative" of phosphacan contains additional chemical moieties not normally a part of the proteoglycan or its peptide backbone. Covalent modifications of the peptide are included within the scope of this invention and may be introduced into the molecule by reacting targeted amino acid residues of the peptide or protein chain with an organic derivatizing agent that is capable of reacting with selected side chains or terminal residues. Additionally, modified amino acids or chemical derivatives of amino acids of phosphacan or fragments thereof, according to the present invention, may contain additional chemical moieties or modified amino acids not normally a part of the protein. The following examples of chemical derivatives are provided by way of illustration and not by way of limitation.

Aromatic amino acids may be replaced with D- or L-naphthylalanine, D- or L-phenylglycine, D- or L-2-thienylalanine, D- or L-1-, 2-, 3- or 4-pyrenylalanine, D- or L-3-thienylalanine, D- or L-(2-pyridinyl)-alanine, D- or L-(3-pyridinyl)-alanine, D- or L-(2-pyrazinyl)-alanine, D- or L-(4-isopropyl)-phenylglycine, D-(trifluoromethyl)-phenylglycine, D-(trifluoromethyl)-phenylalanine, D-p-fluorophenylalanine, D- or L-p-biphenylphenylalanine, D- or L-p-methoxybiphenylphenylalanine, D- or L-2-indole (alkyl)alanine, and D- or L-alkylalanine where alkyl may be substituted or unsubstituted methyl, ethyl, propyl, hexyl, butyl, pentyl, isopropyl, isobutyl, sec-isotyl, isopentyl, nonacidic amino acids, of chain lengths of C1–C20.

Acidic amino acids can be substituted with non-carboxylate amino acids while maintaining a negative charge, and derivatives or analogs thereof, such as the non-limiting examples of (phosphono)-alanine, glycine, leucine, isoleucine, threonine, or serine; or sulfated (for example, -SO$_3$H) threonine, serine, tyrosine.

Other substitutions may include unnatural hydroxylated amino acids may made by combining "alkyl" with any natural amino acid. Basic amino acids may be substituted with alkyl groups at any position of the naturally occurring amino acids lysine, arginine, ornithine, citrulline, or (guanidino)-acetic acid, or other (guanidino)alkyl-acetic acids, where "alkyl" is define as above. Nitrile derivatives (for example, containing the CN-moiety in place of COOH) may also be substituted for asparagine or glutamine, and methionine sulfoxide may be substituted for methionine. Methods of preparation of such peptide derivatives are well known to one skilled in the art.

In addition, any amide linkage the polypeptides can be replaced by a ketomethylene moiety, for example, (—C(=O)—CH$_2$—) for (—(C=O)—NH—). Such derivatives are expected to have the property of increased stability to degradation by enzymes, and therefore possess advantages for the formulation of compounds which may have increased in vivo half lives, as administered by various routes as described herein.

In addition, any amino acid representing a component of the peptides can be replaced by the same amino acid but of the opposite chirality. Thus, any amino acid naturally occurring in the L-configuration (which may also be referred to as the R or S, depending upon the structure of the chemical entity) may be replaced with an amino acid of the same chemical structural type, but of the opposite chirality, generally referred to as the D-amino acid but which can additionally be referred to as the R- or the S-, depending upon its composition and chemical configuration. Such derivatives have the property of greatly increased stability to degradation by enzymes, and therefore are advantageous in the formulation of compounds which may have longer in vivo half lives, when administered by various routes.

Additional amino acid modifications in phosphacan or in a peptide thereof may include the following.

Cysteinyl residues most commonly are reacted with α-haloacetates (and corresponding amines), such as chloroacetic acid or chloroacetamide, to give carboxymethyl or carboxyamidomethyl derivatives. Cysteinyl residues also are derivatized by reaction with bromotrifluoroacetone, α-bromo-β-(5-imidozoyl)propionic acid, chloroacetyl phosphate, N-alkylmaleimides, 3-nitro-2-pyridyl disulfide, methyl 2-pyridyl disulfide, p-chloromercuribenzoate, 2-chloromercuri-4-nitrophenol, or chloro-7-nitrobenzo-2-oxa-1,3-diazole.

Histidyl residues are derivatized by reaction with diethylprocarbonate at pH 5.5–7.0 because this agent is relatively specific for the histidyl side chain. Parabromophenacyl bromide also is useful; the reaction is preferably performed in 0.1M sodium cacodylate at pH 6.0.

Lysinyl and amino terminal residues are reacted with succinic or other carboxylic acid anhydrides, which reverses the charge of the lysinyl residues. Other suitable reagents for derivatizing α-amino-containing residues include imidoesters such as methyl picolinimidate; pyridoxal phosphate; pyridoxal; chloroborohydride; trinitrobenzenesulfonic acid; O-methylisourea; 2,4 pentanedione; and transaminase-catalyzed reaction with glyoxylate.

Arginyl residues are modified by reaction with one or several conventional reagents, among them phenylglyoxal, 2,3-butanedione, 1,2-cyclohexanedione, and ninhydrin. Derivatization of arginine residues requires that the reaction be performed in alkaline conditions because of the high pK$_a$ of the guanidine functional group. Furthermore, these reagents may react with the groups of lysine as well as the arginine ε-amino group.

The specific modification of tyrosyl residues has been studied extensively with particular interest in introducing spectral labels into tyrosyl residues by reaction with aromatic diazonium compounds or tetranitromethane. Most commonly, N-acetylimidizol and tetranitromethane are used to form O-acetyl tyrosyl species and 3-nitro derivatives, respectively.

Carboxyl side groups (aspartyl or glutamyl) are selectively modified by reaction with carbodiimides (R'-N-C-N-R') such as 1-cyclohexyl-3-(2-morpholinyl-(4-ethyl) carbodiimide or 1-ethyl-3-(4-azonia-4,4-dimethylpentyl) carbodiimide. Furthermore, aspartyl and glutamyl residues are converted to asparaginyl and glutaminyl residues by reaction with ammonium ions.

Glutaminyl and asparaginyl residues are deamidated to the corresponding glutamyl and aspartyl residues. Alternatively, these residues are deamidated under mildly acidic conditions. Either form of these residues falls within the scope of this invention.

Derivatization with bifunctional agents is useful for crosslinking phosphacan to a water-insoluble support matrix or to other macromolecular carriers. Commonly used crosslinking agents include, for example, 1,1-bis(diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis-(succinimidyl-propionate), and bifunctional maleimides such as bis-N-maleimido-1,8-octane. Derivatizing agents such as methyl-3-[(p-azidophenyl)dithio]propioimidate yield photoactivatable intermediates that are capable of forming crosslinks in the presence of light. Alternatively, reactive water-insoluble matrices such as cyanogen bromide-activated carbohydrates and the reactive substrates described in U.S. Pat. Nos. 3,969,287; 3,691,016; 4,195,128; 4,247,642; 4,229,537; and 4,330,440 are employed for protein immobilization.

Other modifications include hydroxylation of proline and lysine, phosphorylation of hydroxyl groups of seryl or threonyl residues, methylation of the α-amino groups of lysine, arginine, and histidine side chains (Creighton, supra), acetylation of the N-terminal amine, and, in some instances, amidation of the C-terminal carboxyl groups.

Such derivatized moieties may improve the solubility, absorption, biological half life, and the like. The moieties may alternatively eliminate or attenuate any undesirable side effect of the protein or proteoglycan, and the like. Moieties capable of mediating such effects are disclosed, for example, in *Remington's Pharmaceutical Sciences*, 16th ed., Mack Publishing Co., Easton, PA (1980).

Phosphacan polypeptides of the present invention can be synthesized or preferably recombinantly produced, and optionally purified, to provide commercially useful amounts of a phosphacan polypeptide for use in therapeutic, diagnostic or research applications, according to known method steps. See, for example, Ausubel, F. et al., eds, *CURRENT PROTOCOLS IN MOLECULAR BIOLOGY*, Wiley Interscience, N.Y., (1987, 1992); and Sambrook et al., *MOLECULAR CLONING, A LABORATORY MANUAL*, 2nd edition, Vols. 1–3, Cold Spring Harbor Press, Cold Spring Harbor, N.Y., 1989; Copsey et al., *GENETICALLY ENGINEERED HUMAN THERAPEUTIC DRUGS*, MacMillan Publ., Ltd., Stockton Press, N.Y., (1988); Schulz et al., supra; Creighton, T. E., supra, which references are herein entirely incorporated by reference.

ANTIBODIES TO PHOSPHACAN

Additionally, phosphacan polypeptides according to the present invention can be used to generate polyclonal and/or monoclonal antibodies, anti-idiotype antibodies thereto, or fragments thereof.

Such antibodies may be used in the isolation and purification of phosphacan or a functional derivative thereof.

Such antibodies are also useful for diagnostic and/or therapeutic applications according to known method steps. See, for example, Harlow, E. et al., *ANTIBODIES: A LABORATORY MANUAL*, Cold Spring Harbor Press, Cold Spring Harbor, N.Y., 1988, which is herein entirely incorporated by reference.

Anti-phosphacan antibodies, either polyclonal or monoclonal can be used to diagnose or localize a tumor, most likely in the central nervous system, which produces phosphacan. Furthermore, by monitoring phosphacan levels in appropriate body fluids, such as cerebrospinal fluid, such antibodies are useful in monitoring tumor progression or regression following various forms of therapy such as surgery, chemotherapy, etc.

CLONING AND EXPRESSION OF PHOSPHACAN

Phosphacan may be purified from a tissue source using conventional biochemical techniques, or produced recombinantly in either prokaryotic or eukaryotic cells using methods well-known in the art (Sambrook, J. et al., *MOLECULAR CLONING: A LABORATORY MANUAL*, 2nd Edition, Cold Spring Harbor Press, Cold Spring Harbor, N.Y., 1989, which reference is hereby incorporated by reference in its entirety).

Fusion proteins representing different polypeptide regions in phosphacan may be used to identify regions of the protein that have the desired functional activity (binding, etc.). When combined with the polymerase chain reaction (PCR) method, it is possible and expedient to express in bacteria nearly any selected region of the protein.

To facilitate unidirectional subcloning of the PCR products, sense and antisense oligonucleotides have been designed to include BamH1 recognition sequences at the 5' end and EcoR1 recognition sequences at the 3' end, respectively; appropriately digested PCR products are then be ligated directly into a vector (such as the pGEX-2T vector). Use of this methodology allows construction of vectors and purification of several fusion proteins in less than one month.

The pGEX vector is preferred because the glutathione-S-transferase (GST) fusion proteins can be purified rapidly by binding to glutathione-agarose beads. In addition, because cDNAs are cloned into pGEX-2T, the portion of the fusion protein representing the GST can be cleaved with thrombin and the engineered polypeptide can generally be recovered free of the GST protein which can be removed using glutathione-agarose beads (Ausubel, et al., supra).

Phosphacan, a peptide thereof, or a fusion protein thereof may also be expressed in insect cells using baculovirus expression system. Production of phosphacan or functional derivatives thereof, including fusion proteins, can be performed in insects, for example, by infecting an insect host with a baculovirus engineered to express phosphacan by methods known to those of skill. Thus, in one embodiment, sequences encoding phosphacan may be operably linked to the regulatory regions of the viral polyhedrin protein (Jasny, 1987, *Science* 238:1653). Infected with the recombinant baculovirus, cultured insect cells, or the live insects themselves, can produce the phosphacan or functional derivative in amounts as great as 20 to 50% of total protein production. When live insects are to be used, caterpillars are presently preferred hosts for large scale production according to the invention.

Fragments of phosphacan are purified by conventional affinity chromatography using antibodies, preferably mAbs, that recognize the appropriate regions of phosphacan. The mAbs specific for the most highly conserved regions in phosphacan can be used to purify phosphacan from mixtures.

Such antibodies, including antibodies specific for one or more particular phosphacan peptide epitopes, can be used to diagnose and localize phosphacan producing tumors such as gliomas, glioblastomas, astrocytomas, etc.

According to the present invention, binding of phosphacan proteoglycans, including functional derivatives thereof, may be used to diagnose or treat subjects having a pathology related to neural cell adhesion, cell recognition, and cell interactions in developing nervous tissue, axonal growth, and neuronal differentiation. The compositions of the present invention may also modulate, quantitatively or qualitatively, the binding of phosphacan molecules to a ligand or receptor. The compositions of the present invention are useful in inhibiting or stimulating the binding of phosphacan to N-CAMs, Ng-CAMs, or any other cell adhesion molecules to which phosphacan binds.

To characterize functions of phosphacan, and of different regions of phosphacan, any of a number of assays may be used. These assays may be used routinely to analyze the binding of a phosphacan molecule or a functional derivative thereof to a natural or synthetic binding partner, such as N-CAMs or Ng-CAMs, or antiphosphacan antibodies.

THERAPEUTIC APPLICATIONS OF PHOSPHACAN

The preferred animal subject of the present invention is a mammal. By the term "mammal" is meant an individual belonging to the class Mammalia. The invention is particularly useful in the treatment of human subjects.

The present invention provides for methods of treatment of diseases or disorders associated with abnormal cell adhesion interactions in nervous tissue, or with altered tyrosine phosphatase activation therein. The methods comprise administering to a subject in need of such treatment an effective amount of phosphacan or a functional derivative thereof, that inhibits activation of RPTP molecules or inhibits binding of CAMs by endogenous phosphacan.

Examples of disorders that may be treated or diagnosed according to this invention include, but are not limited to gliomas and glioblastomas. Antibodies to phosphacan are particularly useful for monitoring the therapy of such tumors using conventional or novel therapeutic modalities.

Effective doses of phosphacan for therapeutic uses discussed above may be determined using methods known to one skilled in the art. Effective doses may be determined, preferably in vitro, in order to identify the optimal dose range using various of the methods described herein. In one embodiment, an aqueous solution of phosphacan, or a functional derivative of phosphacan, is administered by intravenous injection. Each dose may range from about 0.001 µg/kg body weight to about 10 mg/kg body weight, or more preferably, from about 0.1 µg/kg to 10 mg/kg body weight. The dosing schedule may vary from once a week to daily depending on a number of clinical factors. Nonlimiting examples of dosing schedules are 3 µg/kg administered twice a week, three times a week or daily; a dose of 7 µg/kg twice a week, three times a week or daily; a dose of 10 µg/kg twice a week, three times a week or daily; or a dose of 30 µg/kg twice a week, three times a week or daily. It may be preferable to administer doses such as those described above by alternate routes, including intravenously or intrathecally. Continuous infusion may also be appropriate. A preferred mode of administration is localized administration using the composition adsorbed to a solid phase such as nitrocellulose membranes or inserted into a slow-release depot device which is implanted into the subject.

Phosphacan or a functional derivative may also be administered in combination with an effective amount of at least one other agent that is, itself, capable of promoting nerve growth or regeneration or otherwise aiding in the general health of the subject. Such agents include anti-infectives, including anti-bacterial, anti-viral and anti-fungal agents, local anesthetics, and analgesics, or a combination thereof.

The phosphacan may be administered in any pharmaceutically acceptable carrier. The administration route may be any mode of administration known in the art, including but not limited to intravenously, intrathecally, subcutaneously, or intracranially by injection into involved tissue, intraarterially, orally, or via an implanted device such as a solid phase device or a depot device to which the compound is bound or from which it is released.

The present invention also provides pharmaceutical compositions comprising phosphacan, or a functional derivative thereof in a pharmaceutically acceptable carrier, in an amount effective to promote nerve regeneration.

Also provided is a pharmaceutical composition comprising an effective amount of phosphacan together with one or more additional agents in a pharmaceutically acceptable carrier. Such additional agents include agents which are known to promote nerve growth or regeneration. Examples of such agents include disinfectants such as antibacterial agents or antiviral agents, anti-fungal agents, anti-inflammatory agents, agents which induce relief from pain.

The pharmaceutical compositions of the present invention may be administered by any means that achieve their intended purpose. Amounts and regimens for the administration of phosphacan, or a derivative thereof, can be determined readily by those with ordinary skill in the clinical art of treating such neurological conditions.

Compositions within the scope of this invention include all compositions wherein the phosphacan proteoglycan, protein, peptide or derivative is contained in an amount effective to achieve its intended purpose. While individual needs vary, determination of optimal ranges of effective amounts of each component is within the skill of the art. Typical dosages comprise 0.0001 to 10 mg/kg/body wt. The preferred dosages comprise 0.01 to 10 mg/kg/body wt.

In addition to the pharmacologically active compounds, the new pharmaceutical preparations may contain suitable pharmaceutically acceptable carriers comprising excipients and auxiliaries which facilitate processing of the active compounds into preparations which can be used pharmaceutically. Suitable formulations for oral administration include hard or soft gelatin capsules, dragees, pills tablets, including coated tablets, elixirs, suspensions, syrups or inhalations and controlled release forms thereof. Preparations which can be administered rectally are suppositories. Suitable injectable solutions include intravenous subcutaneous and intramuscular injectable solutions. The compositions may also be administered in the form of an infusion solution or as a nasal inhalation or spray. Suitable solutions for administration by injection or orally, contain from about 0.01 to 99 percent, preferably from about 20 to 75 percent of active compound(s), together with the excipient. The pharmaceutical formulation for systemic administration according to the invention may be formulated for enteral, parenteral or topical administration. Indeed, all three types of formulation may be used simultaneously to achieve systemic administration of the active ingredient.

The effects of developmentally regulated glycosylation on the ability of phosphacan to bind to neurons, neural cell adhesion molecules, tenascin, and other potential cell surface or extracellular matrix ligands for membrane tyrosine phosphatases are currently being explored. It is possible that developmental changes in glycosylation and in the localization and levels of the extracellular proteoglycan may also serve to modulate the activity of the transmembrane phosphatase.

Thus, the glycosylation of the phosphacan molecule or derivative of the present invention may be important in its biological or pharmaceutical activity. For example, keratan sulfate-containing phosphacans show several different glycosylation variants. CD45 phosphatase has unsulfated chains of keratan sulfate which may be biologically meaningful. Such glycosylation variants may be important relative to isoforms, switching, and binding to target molecules. According to this invention, the phosphacan or derivative may be modified in various ways, either chemically or recombinantly to modify glycosylation. Examples include, but are not limited to: (a) removing chondroitin sulfate using chondroitinase; (b) removing the keratan sulfate using endo-β-galactosidase; (c) removing non-reducing terminal sugars with the appropriate exoglycosidase enzyme, for example, neuraminidase, galactosidase, fucosidase, hexosaminidase, etc.; (d) adding sugars using nucleotide sugar donors and the appropriate glycosyl transferase enzyme; or (e) changing the amino acid sequence to insert or delete amino acid residues which may be glycosylated. See, for example, Kornfeld, R. et al.. (1985) *Annu. Rev. Biochem.* 54:631–664; Rosner, M. R. et al. (1983) *Methods Enzymol.* 83:432–443; Tabas, I. et al. (1983) *Methods Enzymol.* 83:416–429; Schwartz, R. T. et al. (1984) *Trends Bio. Sci.* 9:32–34; Elbein, A. D. (1984) *CRC Crit. Rev. Biochem.* 15:21–49.

Having now generally described the invention, the same will be more readily understood through reference to the following examples which are provided by way of illustration, and are not intended to be limiting of the present invention, unless specified.

EXAMPLE I

MATERIALS AND METHODS

A. Preparation of Peptides and Amino Acid Sequence Analysis

Proteoglycans were isolated from a phosphate buffered saline (PBS) extract of rat brain by immunoaffinity chromatography using the 3F8 or 3H1 mAbs (Rauch et al., 1991, supra).

Chondroitinase and protease digestions, CNBr treatment, electrophoresis, and transfer to ProBlott membranes for N-terminal amino acid microsequencing were performed as described previously (Rauch et al., 1992, supra).

N-terminal amino acid sequences of proteins in solution were obtained after drying on polybrene-coated glass fiber filters.

Internal amino acid sequences were also obtained after transfer of the 3F8 proteoglycan core glycoprotein and a CNBr peptide to nitrocellulose followed by in situ digestion with trypsin or endoproteinase Lys-C (Aebersold, R. H. et al., (1987) *Proc. Natl. Acad. Sci. USA* 84:6970–6974), and by trypsin digestion of the intact 3H1 proteoglycan, in both cases followed by reverse phase HPLC fractionation of the resulting peptides prior to microsequencing of the individual peaks.

B. Generation of Probes by the PCR and Isolation of cDNA Clones

Degenerate oligonucleotide primers based on the N-terminal amino acid sequence of the 3F8 proteoglycan and the sequence of an internal CNBr peptide (FIG. 1) were synthesized with BamHI and Hind III linkers.

An oligo(dT) primed 6-week rat brain λZAPII cDNA library (Stratagene) was used as template for amplification with Taq polymerase (Perkin-Elmer/Cetus), using 50 temperature-step cycles of 94° C. (0.5 min), 55° C. (1.5 min), and 72° C. (5 min).

Agarose-ethidium bromide gel electrophoresis of the PCR reaction products demonstrated a 780 base pair band which was not produced from a control reaction containing only single primers or empty λZAPII vector.

The PCR product was subcloned into pGEM3 and antisense RNA transcripts were prepared for screening of the same cDNA library, as described previously (Rauch et al., 1992, supra).

base pair PCR product used for cDNA library screening was transcribed into digoxigenin-labeled antisense RNA and used for hybridization with Northern blots of mRNA prepared from brain and other tissues (Rauch et al., 1992, supra).

Probes for the cytoplasmic domain of the phosphatase were synthesized by PCR using rat brain cDNA as template, and sense and antisense primers (with Xho I and Hind III linkers) based on amino acid and nucleotide sequences of the first and second phosphatase domains of human PTPζ/β (Krueger et al., supra; Levy et al., supra).

The primers for the first phosphatase domain were:

Sense: 5'-CGAATTCTCGAGGAA$^A_G$TG$^T_G$GA$^T_C$CA$^A_G$TA$^T_C$TGGCCIGCIGA$^T_C$G-3' also designated as [SEQ ID NO:10]

CGAATTCTCGAGAARTGYGAYCARTAYTGGCCNGCGAYG, wherein N is inosine

Antisense: 5'-GCTCTAGAAGCTTGTAGTCTGTGCCTTCCCCACTCAGG-3'; [SEQ ID NO:11]

The primers for the second phosphatase domain were:

Sense: 5'-GCAATTCTCGAGCCTGTGGAAAGATCAAGGGTTGGC-3' [SEQ ID NO:12]

Antisense: 5'-GCAATTAAGCTTATGCTCATCATGAACAATCATAGG-3'. [SEQ ID NO:13]

A probe to the extracellular domain of PTPζ/β (Krueger et al., supra; Levy et al., supra) near the transmembrane region was synthesized by reverse transcription/PCR (Rauch et al., 1992, supra) using 4-day rat brain mRNA and primers designed on the basis of the human sequence:

Sense: [SEQ ID NO:8]
5'-CCCTCGAGGAAGGCATGTATTTGC-3';

Antisense: [SEQ ID NO:9]
5'-GCCTCTAGATTCACCACCACCCACTAAACC-3'.

The 346 base pair PCR product was subcloned into the Xba I and Sma I sites of pGEM7Zf, linearized with Bam HI, and a $^{32}$P-labeled riboprobe was transcribed and used to screen an oligo(dT)/random-primed λZAPII rat brain stem/spinal cord cDNA library (Stratagene). Positive clones were selected for further study only if they gave no PCR product using primers complementary to a sequence in the first phosphatase domain of the transmembrane protein (see below). These were converted to Bluescript plasmids by in vivo excision and used for sequencing.

C. DNA Sequencing

Subclones for sequencing (using Taq polymerase in conjunction with dye-labeled terminators and the Applied Biosystems Model 373A DNA sequencing system) were generated by deletions produced with restriction enzymes, by subcloning of restriction fragments, and by progressive unidirectional exonuclease III deletions.

Sequencing was also performed using synthetic primers corresponding to the ends of previously determined sequences. Both strands of the DNA were sequenced, with sequence alignment and analysis accomplished with the software package from the Genetics Computer Group (Madison, Wis.). The reading frame was verified by N-terminal amino acid sequence data for the core glycoprotein and for peptide fragments derived from it.

D. Northern Blots

As a probe for the N-terminal portion of the 3F8 proteoglycan, the nucleotide sequence from the original 780

The resulting PCR products were subcloned into pGEM, their identity was confirmed by sequencing, and they were then transcribed into digoxigenin-labeled antisense RNA.

EXAMPLE II cDNA Clones Corresponding to the N-terminal Portion of the 3F8 Proteoglycan Identical N-terminal amino acid sequences were obtained from both the native proteoglycan and the core glycoprotein (resulting from chondroitinase treatment) transferred to a ProBlott membrane after SDS-PAGE (FIG. 1). This same N-terminal amino acid sequence was also obtained from two CNBr peptides derived from the core glycoprotein and transferred to ProBlott, having molecular weights of 22 kDa and 40 kDa.

The N-terminal amino acid sequence of an internal 14 kDa CNBr peptide was obtained in a similar manner, and other internal peptide sequences were obtained from in situ trypsin digestion or endoproteinase Lys-C digestion of CNBr peptides or of the entire core glycoprotein transferred to nitrocellulose, followed by reverse phase HPLC of the digestion products. These sequences are shown in FIG. 1.

For cloning the 3F8 proteoglycan, the present inventors initially used mixed oligonucleotide-primed PCR amplification of cDNA, based on amino acid sequences present in the proteoglycan, for synthesis of an unambiguous nucleic acid probe.

The N-terminal sequences of the core glycoprotein and of the 14 kDa CNBr peptide were used for the design of PCR primers as follows:

Sense: 5'-CCGCGGATCCAA(AT/GC)T(T/G)GT(T/G)GA(A/G)GA(A/G)AT(T/G)GGT(T/G)GG-3' also designated as [SEQ ID NO:14]

CCGCGGATCCAARYTNGTNGARGARATNGGNTGG, wherein N is inosine; and

Antisense: 5'-GCTTAAGCTT(A/G)TA(C/T)TG(C/T)TG(C/T)TCIC(GA/TG)AA(A/G)TT(A/G)TT(C/T)TG-3' also designated as [SEQ ID NO:15]

GCTTAAGCTTRTAYTGYTGYTCNCKRAARTTRTTYTG, wherein N is inosine.

This primer combination resulted in the enzymatic amplification of a 780 base pair product using a rat brain cDNA library as template. Dideoxy sequencing demonstrated that both the 3' and 5' ends contained nucleotides encoding the respective proteoglycan amino acid sequences adjacent to those utilized in the primer design.

The cDNA library was divided into aliquots, and lysates from each of these were tested by PCR using new primers based on exact sequences of the original PCR product:

Sense: 5'-TCTCACCAATGACTACTATCTC-3'; [SEQ ID NO:16]

Antisense: 5'-AGTACTTGTCAGTGGAGTTTGG-3'. [SEQ ID NO:17]

The 9 positive eluates which yielded the expected 370 base pair PCR product were each grown on one plate and screened with an antisense RNA transcript of the original PCR product. Supernatants of positive plaques were checked by PCR, and five positive clones from a second screening were converted into Bluescript plasmids by in vivo excision. Two of these (c12 and c21) were used for sequencing.

A sequence of 469 amino acids deduced from a 1.4 kb open reading frame contained the N-terminal amino acid sequence of the 3F8 core glycoprotein as well as all of the CNBr, trypsin-generated and endo Lys-C-generated peptide sequences from the proteoglycan (FIG. 2).

The deduced amino acid sequence, beginning with a 24 amino acid signal peptide, revealed an N-terminal domain of 255 amino acids (residues 38–292) having significant identity to carbonic anhydrases and 93% identity to a carbonic anhydrase domain in the N-terminus of human PTPζ/β (Krueger et al., supra; Levy et al., supra).

The 30 N-terminal amino acids of the 3H1 chondroitin/keratan sulfate proteoglycan were found to be identical to those of the 3F8 proteoglycan, and six internal tryptic peptide sequences also matched those found in sequenced peptides of the 3F8 proteoglycan and/or amino acid sequences deduced from the cDNA clones (FIGS. 1 and 2).

EXAMPLE III

Northern Blot Analyses

An RNA probe corresponding to the cDNA sequence of the extracellular N-terminal carbonic anhydrase domain hybridized with mRNA of 9.5 kb, 8.4 kb, and 6.4 kb from both 4 day old and adult rat brain mRNA. A faint band above 9.5 kb was sometimes seen in early postnatal brain (FIG. 3).

A 160 kDa probable splice variant of RPTPβ has been identified wherein nucleotides 2393 to 4951 are deleted (Levy et al., supra) and may correspond to the 6.4 kb message seen on Northern blots. The 8.4 kb message was not detectable using probes corresponding to either the first or second cytoplasmic phosphatase domains (FIG. 3), suggesting that this mRNA may code for a soluble protein containing only the extracellular portion of the phosphatase.

No message was detected in liver, kidney, muscle, lung, or rat PC12 pheochromocytoma cells. These findings are consistent with the reported limitation of RPTPβ expression to nervous tissue, and with the present inventors' finding that the proteoglycan is synthesized by glia (Milev, P. et al., (1993) Glycobiology 3, 535).

EXAMPLE IV

Identification of an Extracellular Variant of the Phosphatase

The results of Northern analyses suggested that the 3F8 proteoglycan isolated in a PBS extract of brain might represent an extracellular splice variant of the full-length transmembrane RPTP. Reverse transcription/PCR was therefore used to synthesize a probe to a sequence about 0.8 kb upstream of the human RPTPζ/β transmembrane region (corresponding to nucleotides 4050–4380 in FIG. 2). This PCR product was subcloned into pGEM and used as template to transcribe a riboprobe for library screening.

As expected, on Northern analysis, it hybridized with only the 9.5 kb and 8.4 kb messages.

Two cDNA clones (pBSP3 and pBSP4) were identified which gave no PCR product using primers corresponding to sequences in the first phosphatase domain (which should be absent from the putative extracellular splice variant) These clones were therefore considered good candidates for further study.

Restriction analysis and sequencing demonstrated that clone pBSP4 overlapped at its 5' end with the N-terminal sequence of the proteoglycan obtained from clones c12 and c21 (see final page of FIG. 2). Both clones contained identical 3'-untranslated sequences preceded by a stop codon at the putative 3' splice site of RPTPβ (Levy et al., supra), and may therefore represent an alternative splicing product corresponding to the 8.4 kb mRNA seen on Northern blots. The rat amino acid sequence had 76% identity to the human sequence, whereas the 3'- and 5'-untranslated regions had no identity.

Northern analysis was performed using a riboprobe transcribed from a subcloned EcoRI fragment from the beginning of the 3'-untranslated region (nucleotides 5034–5820). The results indicated that this probe hybridized to the 8.4 kb and, very weakly, to the 9.5 kb messages (FIG. 3). These results suggested that: (1) the extracellular proteoglycan may be the major product of the phosphatase gene (or a closely related gene) expressed in rat brain, and that the 3'-untranslated regions may not be identical in the three mRNAs.

That the extracellular proteoglycan does in fact have a different 3'-untranslated region has been demonstrated by sequencing clones for the full-length rat PTPase.

DISCUSSION OF EXAMPLES I–IV

The studies reported above demonstrated that the 3F8 and 3H1 proteoglycans of brain, which have been named "phosphacan", are glycosylation variants and possible extracellular splice variants of a receptor-type transmembrane protein tyrosine phosphatase designated PTPζ (Krueger et al., supra) and RPTPβ (Levy et al., supra).

The proteoglycan contains an N-terminal domain homologous to carbonic anhydrases. At least seven mammalian carbonic anhydrase isozymes are known, and the highest level of identity (32%) of phosphacan is with carbonic anhydrase VI, a protein secreted by salivary glands (Aldred, P., et al. (1991) *Biochemistry* 30, 569–575).

However, because a catalytically obligatory zinc ion is bound to three essential histidine residues in carbonic anhydrases, whereas, in both rat phosphacan and human receptor PTPζ/β, two of these amino acid residues have been changed to threonine and glutamine (FIG. 2), it is unlikely that this proteoglycan can function as a catalytically active carbonic anhydrase (Krueger et al., supra).

Based on the general definition of fibronectin type III repeats as about 90-residue modules characterized by conserved tryptophan and tyrosine residues in their N- and C-terminal halves, respectively, but lacking conserved cysteine residues, such a domain can be identified in phosphacan (residues 312–391; including Trp-332 and Tyr-384).

The amino acid sequence deduced from the presently described cDNA clones, corresponding to a 173 kDa mature protein with a calculated pI of 4.32, has 76% identity to the extracellular portion of the 252 kDa human transmembrane protein tyrosine phosphatase RPTPζ/β, and a much lower degree of identity (27%) with the extracellular portion of another receptor tyrosine phosphatase (RPTPγ) which also contains a carbonic anhydrase-like domain (Barnea, G. et al., (1993) *Mol. Cell. Biol.* 13:1497–1506).

Of the 36 Ser-Gly or Gly-Ser dipeptides in phosphacan, all of the serine residues which could serve as potential chondroitin sulfate attachment sites are located in the large serine-rich and threonine-rich (approximately 23%) domain outside of the carbonic anhydrase homology region. The potential sites consisting of serine-glycine sequences with a closely preceding or immediately following acidic amino acid, which sites are most likely to be utilized, are provides evidence that RPTPs may also mediate cell interactions through heterophilic mechanisms and may be involved in axonal pathfinding and stabilization (Tian, S.-S. et al., (1991) *Cell* 6Y:675–685; Yang, X. et al., (1991) *Cell* 67:661–673).

In situ hybridization histochemistry demonstrated a high level of expression of phosphacan in the ventricular zone and other areas of cell proliferation in the embryonic rat CNS. In postnatal cerebellum, phosphacan is synthesized by glial cells such as the Golgi epithelial cells, from which the Bergmann glia fibers project into the molecular layer of the cerebellum.

The data presented here, in combination with the knowledge that staining of the 3F8 and 3H1 proteoglycans with mAbs is most intense in the molecular layer, indicate that phosphacan may play important roles in nervous tissue histogenesis.

EXAMPLE V

MEASUREMENT OF PHOSPHACAN EXPRESSION

Rat C6 glioma cells or human cells such as U-373 MG glioblastoma (grade III astrocytoma) cells may be used. These cells are available from the ATCC. Cells are propogated in one of several media, including:

(1) Ham's F10 medium (82.5%) supplemented with horse serum (15%) and fetal bovine serum (2.5%); and
(2) Eagle's MEM with nonessential amino acids, 1 mM sodium pyruvate and Earle's BSS (90%) supplemented with 10% fetal bovine serum.

mRNA is prepared as described by Rauch et al. (supra). Northern blots are probed with digoxigenin-labeled riboprobe to the carbonic anhydrase domain of phosphacan.

Using the above methods, Northern blots demonstrated that both tumor cell lines (C6 rat glioma cells and human

| serine-595 | (DDSSGSS) (Asp Asp Ser Ser Gly Ser Ser) | [SEQ ID NO: 18] |
| serine -1005 | (DGEWSGAG) (Asp Gly Glu Trp Ser Gly Ala Gly) | [SEQ ID NO: 19] |
| serine -1549/1551 | (DEESGSGQG) (Asp Glu Glu Ser Gly Ser Gly Gln Gly) | [SEQ ID NO: 20], and |
| serine -645 | (EDSAPSGSEE) (Glu Asp Ser Ala Pro Ser Gly Ser Glu Glu) | [SEQ ID NO: 21]. |

These five sites are sufficient to accommodate the calculated four chondroitin sulfate chains in the 3F8 proteoglycan.

Potential attachment sites for the keratan sulfate chains in the 3H1 proteoglycan are less certain. Some or all of the keratan sulfates are linked through novel mannosyl-O-ser/thr linkages which the present inventors' laboratories have previously described in the chondroitin sulfate proteoglycans of brain (Krusius, T. et al., (1986) *J. Biol. Chem.* 261:8237–8242; Krusius, T. et al., (1987) *Biochem. J.* 245:229–234).

The 3F8/3H1 proteoglycans appear to represent glycosylation variants of the same protein, and, considered together, account for 15–20% of the total soluble chondroitin sulfate proteoglycan protein in early postnatal and adult rat brain, respectively. Therefore, phosphacan represents a major fraction of brain proteoglycans, like neurocan which accounts for ~20% of the soluble proteoglycan protein and is the only other well-characterized chondroitin sulfate proteoglycan present at similarly high levels in brain.

RPTPs containing immunoglobulin-like and fibronectin type III-like repeats have been shown to mediate cell-cell adhesion by homophilic binding of their extracellular domains (Gebbink, M. F. B. G. et al., (1993) *J. Biol. Chem.* 268:16101–16104; Brady-Kalnay, S. M. et al., (1993) *J. Cell Biol.* 122:961–972. The ability of phosphacan to bind to N-CAM, Ng-CAM, and tenascin (Grumet et al., supra; Milev, P. et al., (1993) *J. Neurochem.* 61 (Suppl.):S110C)

U-373 MG glioblastoma cells) expressed message for phosphacan (8.4 kb band), although, as compared to brain, in which this message is predominant, the 6.4 kb "short" form of the transmembrane phosphatase was the major band in mRNA from the tumor cell lines. Furthermore, human gliomas and glioma cell lines expressed the phosphacan proteoglycan, as determined using polyclonal antibodies.

The references cited above are all incorporated by reference herein, whether specifically incorporated or not.

Having now fully described this invention, it will be appreciated by those skilled in the art that the same can be performed within a wide range of equivalent parameters, concentrations, and conditions without departing from the spirit and scope of the invention and without undue experimentation.

While this invention has been described in connection with specific embodiments thereof, it will be understood that it is capable of further modifications. This application is intended to cover any variations, uses, or adaptations of the invention following, in general, the principles of the invention and including such departures from the present disclosure as come within known or customary practice within the art to which the invention pertains and as may be applied to the essential features hereinbefore set forth as follows in the scope of the appended claims.

What is claimed is:

1. An isolated phosphacan proteoglycan molecule or a functional derivative thereof which derivative binds noncovalently to the adhesion molecule Ng-CAM or N-CAM, wherein, when said proteoglycan is one which naturally occurs, said proteoglycan is substantially free of other proteins or proteoglycans with which it is natively associated.

2. A proteoglycan molecule according to claim 1, which does not occur in nature.

3. A proteoglycan molecule according to claim 1, which occurs in nature and is substantially free of other proteins or proteoglycans with which it is natively associated.

4. A phosphacan proteoglycan molecule according to claim 1 having the amino acid sequence SEQ ID NO: 7, or a functional derivative thereof.

5. A core glycoprotein of the proteoglycan of claim 4.

6. A composition comprising an isolated proteoglycan or functional derivative according to claim 4, or a recombinant phosphacan proteoglycan, core protein or core glycoprotein or functional derivative substantially free of other proteins or proteoglycans with which phosphacan is natively associated, adsorbed or immobilized on a solid phase.

7. A proteoglycan molecule according to claim 1 having the biological activity of inhibiting neurite outgrowth.

8. A core glycoprotein of the proteoglycan of claim 1.

9. A composition comprising an isolated proteoglycan or functional derivative according to claim 1, or a recombinant phosphacan proteoglycan, core protein or core glycoprotein or functional derivative substantially free of other proteins or proteoglycans with which phosphacan is natively associated, adsorbed or immobilized on a solid phase.

10. A phosphacan proteoglycan molecule according to claim 1, which is a mammalian phosphacan.

11. A proteoglycan molecule according to claim 10, wherein said mammalian phosphacan is murine, bovine, ovine, human, rat, porcine, equine, canine, feline or caprine phosphacan.

12. A proteoglycan molecule according to claim 10, wherein said mammalian phosphacan is rat phosphacan.

13. A proteoglycan molecule according to claim 10, wherein said mammalian phosphacan is human phosphacan.

14. The proteoglycan of claim 1, 2, 3 or 10 which binds to a neuron.

15. The proteoglycan of claim 1, 2, 3 or 10 which binds noncovalently to a cell adhesion molecule.

16. The proteoglycan molecule of claim 15 in which the cell adhesion molecule is N-CAM.

17. The proteoglycan molecule of claim 15 in which the cell adhesion molecule is Ng-CAM.

18. A recombinant phosphacan proteoglycan, or a core protein or core glycoprotein of phosphacan proteoglycan, or a functional derivative of said proteoglycan, protein or glycoprotein, which derivative binds noncovalently to the adhesion molecule Ng-CAM or N-CAM, said proteoglycan, protein or glycoprotein substantially free of other proteoglycans, proteins or glycoproteins with which phosphacan is natively associated.

19. A proteoglycan, protein or glycoprotein according to claim 18 wherein said phosphacan is a mammalian phosphacan.

20. A proteoglycan, protein or glycoprotein according to claim 19 wherein said mammalian phosphacan is human phosphacan.

21. A proteoglycan, protein or glycoprotein according to claim 18 having the amino acid sequence SEQ ID NO:7, or a functional derivative thereof.

22. The proteoglycan, protein or glycoprotein of claim 18 which binds to a neuron.

23. The proteoglycan, protein or glycoprotein of claim 18 which binds noncovalently to a cell adhesion molecule.

24. The proteoglycan, protein or glycoprotein of claim 23 in which the cell adhesion molecule is N-CAM.

25. The proteoglycan, protein or glycoprotein of claim 23 in which the cell adhesion molecule is Ng-CAM.

26. The proteoglycan, protein or glycoprotein according to claim 18 having the biological activity of inhibiting neurite outgrowth.

27. An isolated protein or glycoprotein encoded by a DNA molecule having the nucleotide sequence SEQ ID NO:6 or by a DNA molecule which hybridizes with DNA having the nucleotide sequence SEQ ID NO:6.

28. A recombinant proteoglycan, protein or glycoprotein encoded by a DNA molecule having the nucleotide sequence SEQ ID NO:6 or by a DNA molecule which hybridizes with DNA having the nucleotide sequence SEQ ID NO:6.

* * * * *